United States Patent
Collins

(10) Patent No.: US 9,894,887 B2
(45) Date of Patent: Feb. 20, 2018

(54) SYSTEM FOR REMOTELY MONITORING A FEED ENVIRONMENT

(71) Applicant: Wilson Collins, Atlanta, GA (US)

(72) Inventor: Wilson Collins, Atlanta, GA (US)

( * ) Notice: Subject to any disclaimer, the term of this patent is extended or adjusted under 35 U.S.C. 154(b) by 0 days.

(21) Appl. No.: 15/006,786

(22) Filed: Jan. 26, 2016

(65) Prior Publication Data
US 2017/0208780 A1  Jul. 27, 2017

(51) Int. Cl.
| A01K 53/00 | (2006.01) |
| H04W 4/00 | (2018.01) |
| A01K 29/00 | (2006.01) |
| A01K 5/02 | (2006.01) |
| A01K 47/06 | (2006.01) |
| A01K 47/00 | (2006.01) |
| G01N 19/10 | (2006.01) |

(52) U.S. Cl.
CPC .............. *A01K 53/00* (2013.01); *A01K 5/02* (2013.01); *A01K 29/005* (2013.01); *A01K 47/06* (2013.01); *H04W 4/005* (2013.01); *A01K 47/00* (2013.01); *G01N 19/10* (2013.01)

(58) Field of Classification Search
None
See application file for complete search history.

(56) References Cited

U.S. PATENT DOCUMENTS

| 6,910,941 | B2 | 6/2005 | Bromenshenk et al. |
| 2009/0114211 | A1* | 5/2009 | Homyk ..................... F24J 2/085 126/578 |
| 2013/0002443 | A1* | 1/2013 | Breed ................... G01J 5/0846 340/686.1 |
| 2013/0284105 | A1* | 10/2013 | Han ........................ A01K 61/02 119/230 |
| 2014/0267705 | A1* | 9/2014 | Hankins .................... A01K 5/02 348/143 |
| 2015/0077244 | A1* | 3/2015 | Lyman ................. G08B 25/016 340/539.12 |
| 2016/0198246 | A1* | 7/2016 | Gurumohan ............. H04Q 9/00 340/870.02 |

* cited by examiner

Primary Examiner — Leon-Viet Nguyen
(74) Attorney, Agent, or Firm — Taylor English Duma LLP

(57) ABSTRACT

A remote monitoring system and a method of remotely monitoring a feed environment that can sense feed stored within a filled container. The remote monitoring system can be configured to determine a distance between a level sensor and a top feed surface of the feed and to wirelessly send feed level data and, optionally, environmental data, to a communication device of a user.

17 Claims, 17 Drawing Sheets

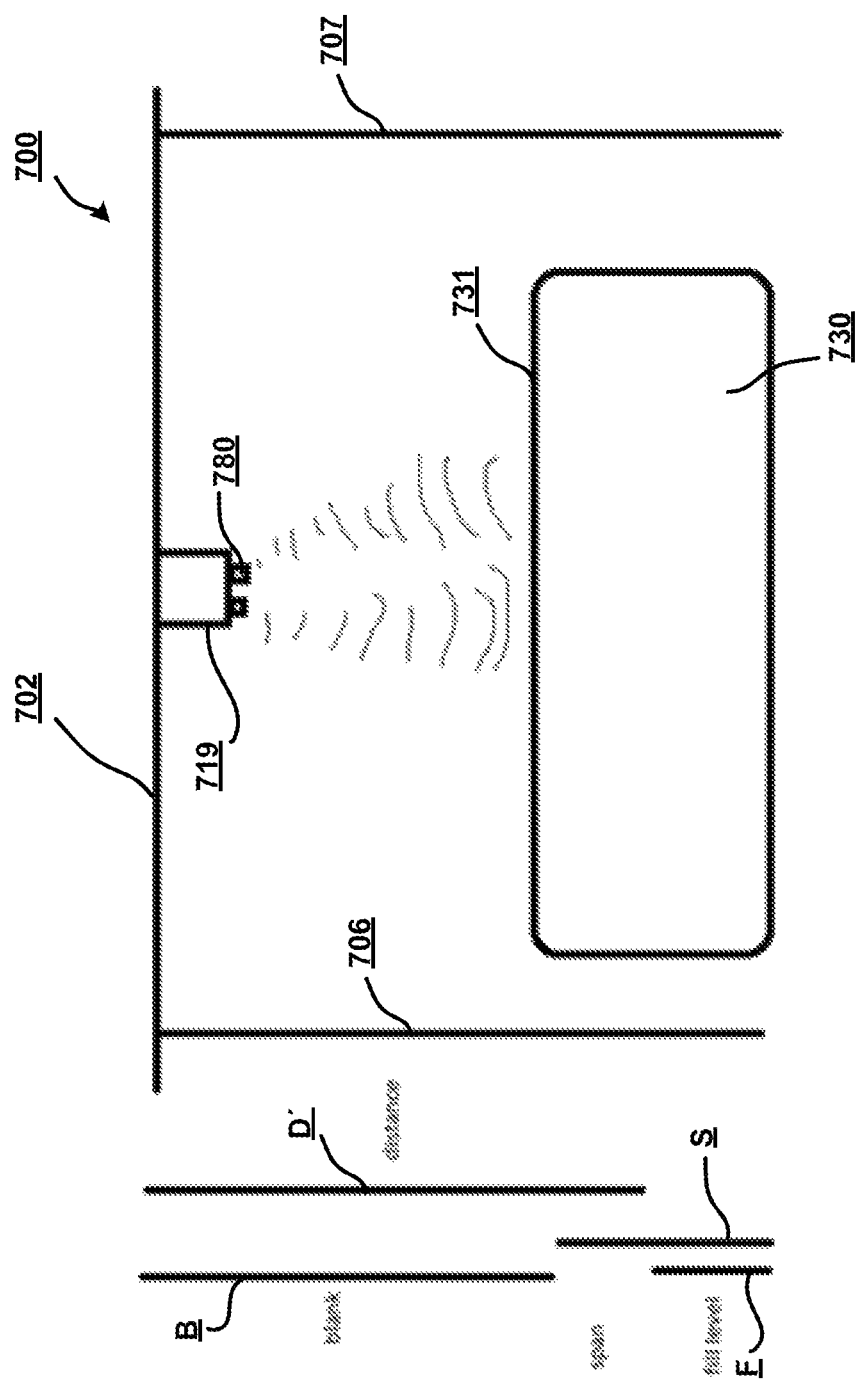

SYSTEM FOR REMOTELY MONITORING A FEED ENVIRONMENT

FIELD

This disclosure relates to a remote monitoring system. More specifically, this disclosure relates to a system for remotely monitoring an environment in which organisms feed.

BACKGROUND TECHNOLOGY

Honey bees play an important role in the earth's ecosystem. According to one source, bees pollinate 15 to 30% of all food eaten by United States consumers, with an economic benefit estimated as high as $117 billion annually. As to the honey that bees produce, the U.S. Department of Agriculture indicated that in 2002, more than $130 million of raw honey produced in the United States.

In the practice of beekeeping, bees are fed with pre-mixed sugar water, which is placed in a container, such as a 55-gallon drum, which can be placed a certain distance, typically around 24 meters (80 ft.) from managed beehives. Estimating feed rate (consumption) is challenging and remote site visits can routinely reveal anything from hardly any drop in the level of sugar water to a completely empty drum for some unknown time. One skilled in the art will appreciate that having the ability to check, for example and without limitation, the sugar water drum level remotely within a matter of seconds would not only save time by not having to drive to a remote site but also would save automobile fuel, thus minimizing honey manufacturing costs. Furthermore, beehives need to be kept dark and temperature-controlled. If any light level other than zero is present inside a beehive, it means that the hive has been breached by the outside—usually either by an animal looking for food or by vandals. Therefore, it would also be advantageous to remotely verify continued darkness inside a hive to quickly address the event of a beehive breach.

SUMMARY

Disclosed is a remote monitoring system and a method of remotely monitoring a feed environment. In one aspect, the remote monitoring system can be configured to sense feed stored within a filled container. In this aspect, the feed has a top feed surface when it is stored in the container. In one aspect, the remote monitoring system can comprise a local module that can be configured to be suspended above the filled container. In this aspect, it is contemplated that the local module can comprise a local microcontroller, a feed level sensor electrically coupled to the local microcontroller, and communication unit electrically coupled to the local microcontroller. In one aspect, the feed level sensor can be configured to determine a distance between the level sensor and the top feed surface of the feed. In another aspect, the communication unit can be configured to exchange data with the local microcontroller and to wirelessly send data to a communication device of a user.

In a further aspect, the method of remotely monitoring feed stored within a filled container can comprise generating feed level data from a sensed level of feed stored within a filled container and transmitting feed level data over a first communication link to a communication device of a user. In one aspect, the method of remotely monitoring feed can further comprise measuring environmental conditions at the local location of the filled container measured and, optionally, environmental conditions at a location remote from the container.

Various implementations described in the present disclosure can include additional systems, methods, features, and advantages, which can not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

FIG. 10C is a schematic diagram showing parameters in feed height determinations in a solid feed environment such as that illustrated in FIGS. 10A and 10B.

DETAILED DESCRIPTION

Figure 1:
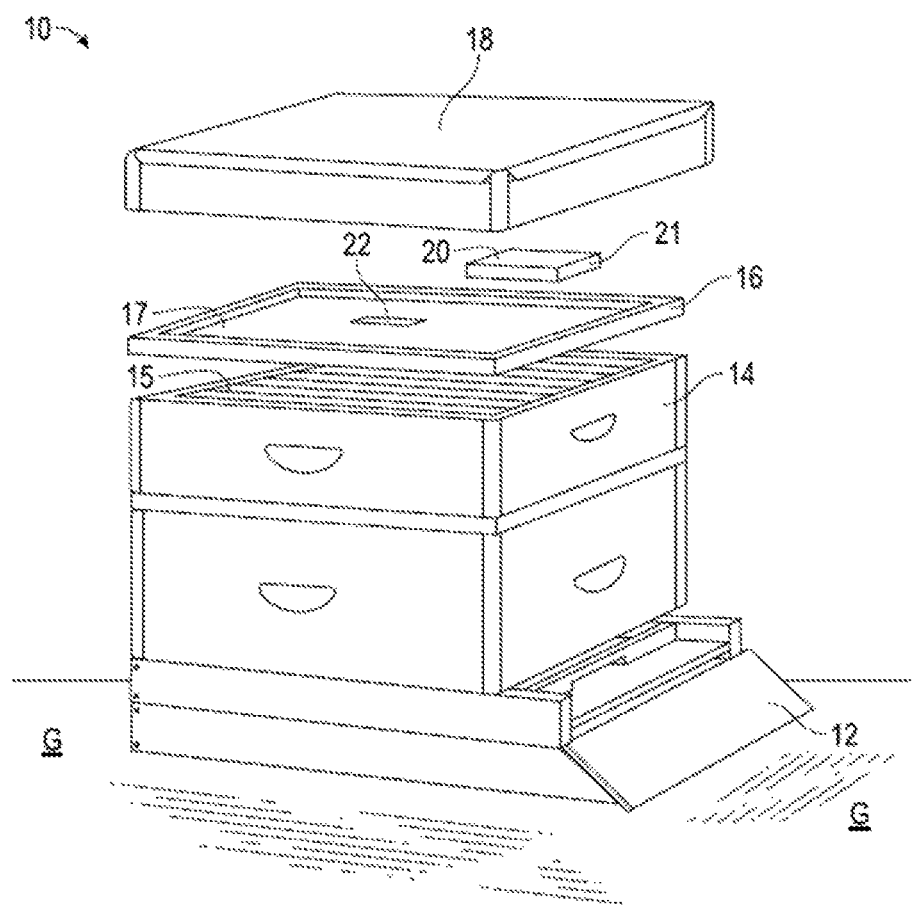
FIG. 1 is a partially-exploded perspective view of a beehive having a conventional construction, except showing a remote module (shown as a slave module), positioned between inner and outer covers of the beehive.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a transmitter" can include two or more such transmitters unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "could," "might," or "can," unless specifically stated otherwise, or otherwise understood within the context as used, is generally intended to convey that certain aspects include, while other aspects do not include, certain features, elements and/or Steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Unless specifically stated otherwise, and as may be apparent from the following description and claims, it should be appreciated that throughout the speciation descriptions utilizing terms such as "processing," "computing, calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices. In a similar manner, the term "processor" may refer to any device or portion of a device that processes electronic data from registers and/or memory to transform that electronic data into other electronic data that may be stored in registers and/or memory. A "computing platform" may comprise one or more processors As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, and apparatuses. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational Steps to be performed on the computer or other programmable apparatus to produce a computer-implemented process such that the instructions that execute on the computer or other programmable apparatus provide Steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

It is contemplated that the processor or computer of the present application can operate in a networked environment using logical connections to one or more remote computing devices. By way of example, a remote computing device can be a personal computer, portable computer, a server, a router, a network computer, a peer device or other common network node, and so on. Logical connections between the processor or computer and a remote computing device can be made via a local area network and a general wide area network. Such network connections can be through a network adapter. It is further contemplated that such a network adapter can be implemented in both wired and wireless environments, which are conventional and commonplace in offices, enterprise-wide computer networks, intranets, and the Internet.

It is recognized that programs and components reside at various times in different storage components of the computing device, and are executed by the data processor(s) of the computer. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

In one aspect, disclosed is a remote monitoring system, comprising a local module, the local module configured to be suspended above a container fillable with feed, the feed when present in the container having a top feed surface. The local module comprises a local microcontroller, a feed level sensor electrically coupled to the local microcontroller, the feed level sensor configured to determine a distance between the level sensor and the top feed surface, and a communication unit, such as a cellular modem, electrically coupled to the local microcontroller, the communication unit being configured to exchange data with the local microcontroller and to wirelessly send data to a communication device of a user. It would be understood by one of skill in the art that the disclosed remote monitoring system is described in but a few exemplary embodiments among many. No particular terminology or description should be considered limiting on the disclosure or the scope of any claims issuing therefrom.

In another aspect of the current disclosure, the local module of the remote monitoring system can further include a renewable power unit electrically coupled to the local microcontroller and at least one solar panel electrically coupled to the renewable power unit. The renewable power unit can comprise a trickle charger, the trickle charger having a charger input and a charger output, the charger input connected to the at least one solar panel, a renewable power source having a source input and a source output, the source input connected to the charger output, and a dc-to-dc converter having a converter input and a converter output, the converter input connected to the source output, the converter output connected to the local microcontroller.

In another aspect of the current disclosure, the local module can further comprise a receiver and a local temperature-and-humidity sensor electrically coupled to the communication unit, and the remote monitoring system can further comprise a remote module configured for placement at a location remote from the local module, the remote module comprises a remote microcontroller, a light sensor electrically coupled to the remote microcontroller, and a transmitter electrically coupled to the remote microcontroller, the transmitter configured to communicate with the receiver. The remote module can further comprise a remote temperature-and-humidity sensor coupled to the remote microcontroller.

In another aspect of the current disclosure, a method of remotely monitoring a feed environment comprises the steps of generating feed level data from a sensed level of feed stored within a container, and causing a transmission of the feed level data over a first communication link to a communication device of a user. The transmission of feed level data can comprise the steps of comparing the feed level data to a predetermined threshold level, and conditioning the transmission of feed level data on the inclusion of a value in the feed level data that is less than the predetermined threshold level. Such transmission can also be triggered the receipt of a message from the sender, and sending a reply communication to the sender, the reply communication including the feed level data.

FIG. 1 illustrates a beehive 10 used by beekeepers to manage bee colonies and having a conventional construction, except for the presence of a remote module 20, positioned between an inner cover 16 and an outer cover 18, constructed according to an embodiment of the present disclosure and to be described in detail later herein. The beehive 10 is shown having several components not material to the present disclosure and which are therefore not described. FIG. 1 illustrates an example of a "remote location," as that term is used in the present disclosure. Beehive 10 can incorporate several conventional components including a stand 12 resting on a ground G, and an enclosure 14 for containing a plurality of frames 15 that facilitate the bees' construction of honeycombs. The inner cover 16 is positioned atop the enclosure 14, and the inner cover 14 has an upper surface 17 into which an aperture 22 is formed. Outer cover 18 can be further provided to protect the internal hive space from weather conditions. The remote module 20 can have an outer case 21, which can have an open top or a lid, depending on design preference. As shown in FIG. 1, the remote module 20 can be simply placed on the upper surface 17 of the inner cover 16. Module 20 can be placed within the hive in any other suitable manner, including attaching it to an inner wall of the outer cover 18.

FIGS. 2-10 illustrate particular components, modules, instructions, engines, etc. according to various examples as described herein. In different implementations, more, fewer, and/or other components, modules, instructions, engines, arrangements of components/modules/instructions/engines, etc. can be used according to the teachings described herein. In addition, various components, modules, engines, etc. described herein can be implemented as instructions stored on a computer-readable storage medium, as hardware modules, as special-purpose hardware (e.g., application specific hardware, application specific integrated circuits (ASICs), as embedded controllers, hardwired circuitry, etc.), or as some combination or combinations of these.

Figure 2:
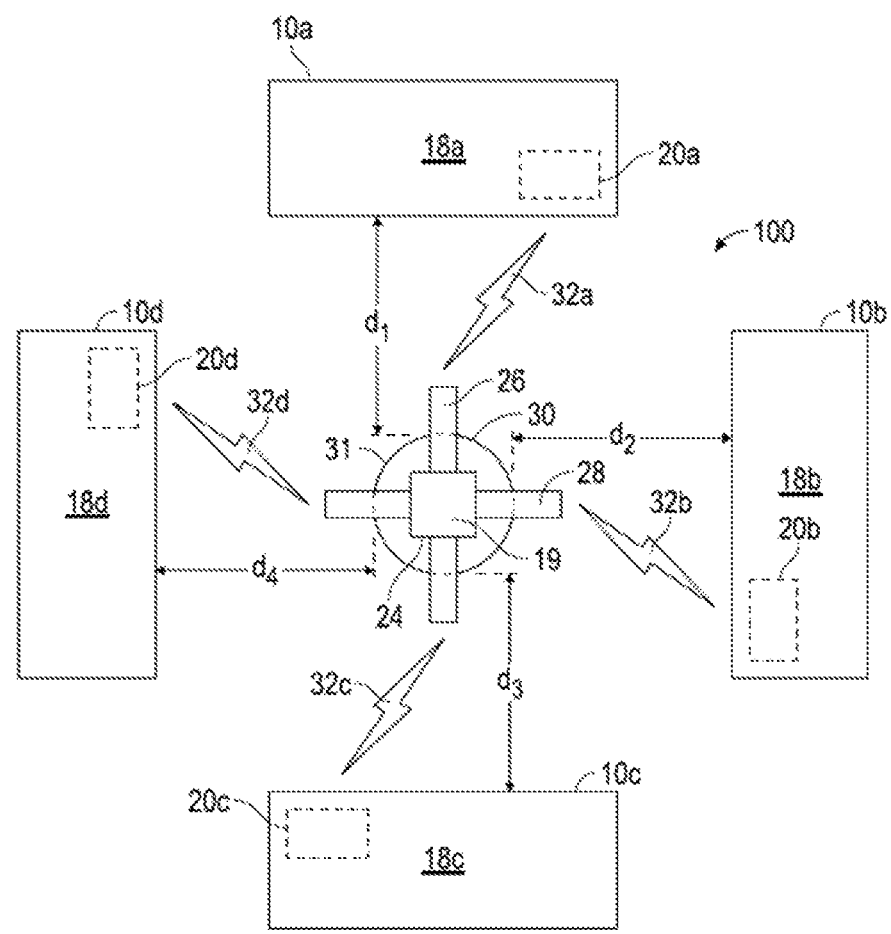
FIG. 2 is a top view of a remote monitoring system for a feeding environment for bees.

FIG. 2 illustrates a top view of a remote monitoring system 100 integrated into a feed environment, here a feed environment for bees, with the system 100 shown constructed according to one embodiment of the present disclosure. Though the system 100 is discussed principally in the context of liquid feed for bees, it can also be employed for solid feed eaten by different animals, to be described with regard to FIGS. 10A and 10B. System 100 comprises a local (master) module 19, shown encased in an enclosure or housing 24 that is supported by cross-members 26, 28, which rest on a rim 31 of a feed container 30. The container 30 can be a barrel, a 55-gallon drum, or any other receptacle having an opening accessible by bees and that can contain a suitable quantity of liquid feed for the bees. The container 30 and local module 19 are shown centrally positioned with respect to four beehives 10a,10b,10c,10d, and spaced from the beehives by respective distances $d_1$, $d_2$, $d_3$, $d_4$. Typically, beehives are spaced from a feeding container by a distance of approximately 24 m (80 ft.), though with more than one hive 10, it is not essential that all hives 10 be spaced equidistantly from the container 30. Furthermore, in an embodiment constructed according to the present disclosure, the local module 19 can communicate with one or more local modules over a distance of approximately 100 m (328 ft.), in a manner to be described herein.

Referring again to FIG. 2, system 100 also comprises one or more remote (slave) modules 20a,20b,20c,20d, respectively housed in beehives 10a,10b,10c,10d beneath corresponding outer covers 18a,18b,18c,18d, in the manner exemplified in FIG. 1. Although FIG. 2 shows four hives with four associated modules, the quantity of such items is not important and is provided only to illustrate that a local module can communicate with more than one remote module. The modules 19, 20 communicate with one another in a master-slave architecture over a radio frequency (RF) band, which may be a 2.4 GHz ISM (Industrial, Scientific, and Medical) band, although the disclosure of a particular RF band herein is not to be considered limiting, as other frequencies may be used. By way of example, as disclosed herein, local module 19 functions as the master module and remote module 20 functions as the slave module. However, it is contemplated that the roles could be reversed such that the local module 19 would function as a slave module and the remote module 20 as the master module. It is also contemplated that system 100 can employ only a master module, without slave modules, if it is desired only to take feed level readings at container 30 and not any readings of conditions within the beehives 10a,10b,10c,10d.

FIG. 2 illustrates wireless communication links 32a,32b, 32c,32d between the local module 19, on one hand, and corresponding remote modules 20a,20b,20c,20d, on the other hand. In a manner to be explained herein, local module 19 is configured and programmed to wirelessly communicate with those remote modules 20a,20b,20c,20d.

Figure 3:
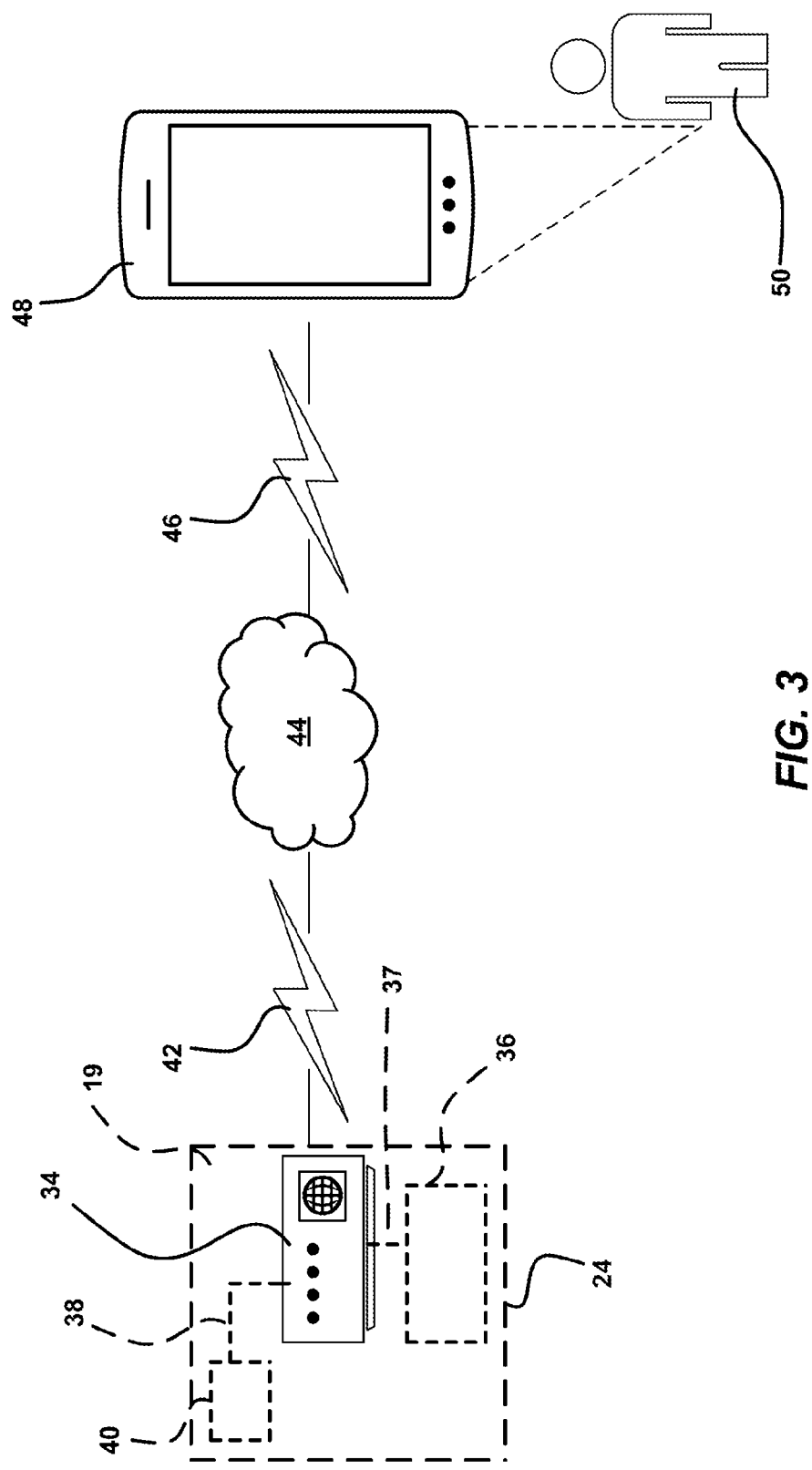
FIG. 3 illustrates an exemplary schematic diagram of an environment through which data is exchanged between a cellular modem in a master module, constructed according to one embodiment of the current disclosure, and an electronic communication device of an end user.

FIG. 3 illustrates additional communication links through which system 100 operates. Specifically, each master module (here, local module 19) comprises a communication unit, such as a cellular modem 34, configured to exchange data, via communication link 37, with a local microcontroller 36 in the local module 19. Cellular modem 34 also shares a communication link 38 with local radio 40, also located in the local module 19, the local radio 40, in one aspect of the present disclosure, receiving communications from a remote module 20 via one of the communication links 32a,32b,32c, 32d (shown in FIG. 2), thus functioning as a receiver. The local microcontroller 36 and the local radio 40 communicate with one over a serial peripheral interface (SPI), which allows the local microcontroller 36 and the local radio 40 to communicate with one another in full duplex mode. Cellular modem 34 wirelessly sends data from an antenna (shown in FIG. 8), across communication link 42, and then to a network 44, which is connected via another communication link 46 to a communication device, such as a smartphone 48, of a user 50. Depending on the form of communication sent, the communication device 48 used need not be limited to a smartphone but could comprise laptop computers and tablets, among other devices capable of electronically retrieving communicated information. The communication links shown in FIGS. 2 and 3 represent a network or networks that can comprise hardware components and computers interconnected by communications channels that enable sharing of resources and information. The network can comprise one or more of a wired, wireless, fiber optic, or remote connection via a telecommunication link, an infrared link, a radio frequency link, a cellular link, a Bluetooth® link, or any other suitable connectors or systems that provide electronic communication. The network can comprise intermediate proxies, routers, switches, load balancers, and the like. The paths followed by the network between the devices as depicted in FIGS. 2 and 3 represent the logical communication links between a remote module 19, the local radio 40, the local microcontroller 36, the cellular modem 34, and the communication device (smartphone) 48, not necessarily the physical paths or links between and among the devices.

FIGS. 4-7 illustrate a local module assembly 51 positioned relative to liquid feed 52 within the container 30, as well as instrumentation by which local module 19 detects the level of the liquid feed 52 within the container 30. In this manner, local module 19 is suspended above the container 30 containing the liquid feed 52.

Figure 4:
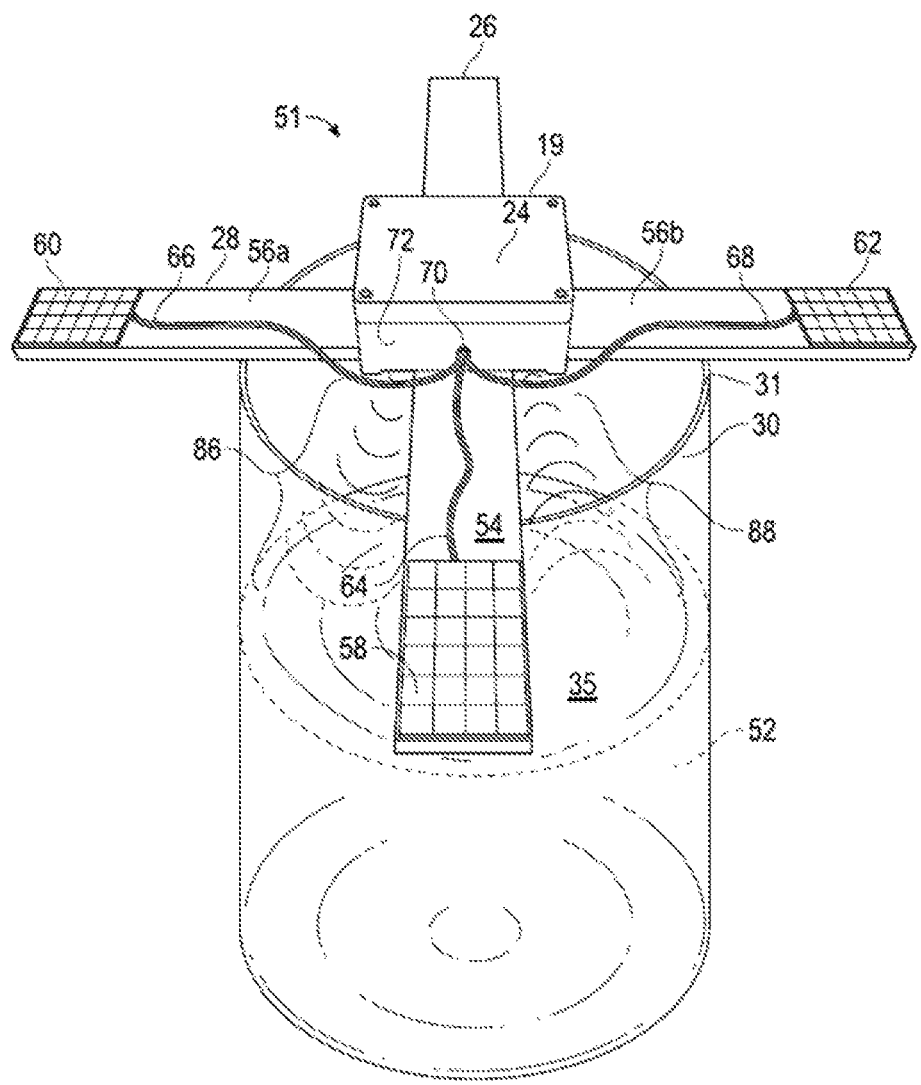
FIG. 4 is a perspective view of an assembly showing a local module (shown as a master module), associated solar panels for charging a power supply in that module positioned atop an open container of liquid feed for bees, and showing the transmission of ultrasonic pulses to measure the level of liquid feed within the container.

Referring to FIG. 4, assembly 51 comprises the local module 19, encased within its housing 24, supported by the cross-members 26,28 as described previously. Cross-member 26 has an upper surface 54, while cross-member 28 has upper surfaces 56a,56b. Assembly 51 also comprises at least one solar panel, which can be an arrangement of three solar panels 58,60,62 supported by and attached to upper surfaces 54,56a,56b, respectively. The solar panels 58,60,62 are electrically coupled to a renewable power unit (FIG. 8) inside the enclosure 24 via wires 64,66,68, respectively, which run from solar panels 58,60,62 to an aperture 70 formed into a sidewall 72 of the local module housing 24.

Figure 6:
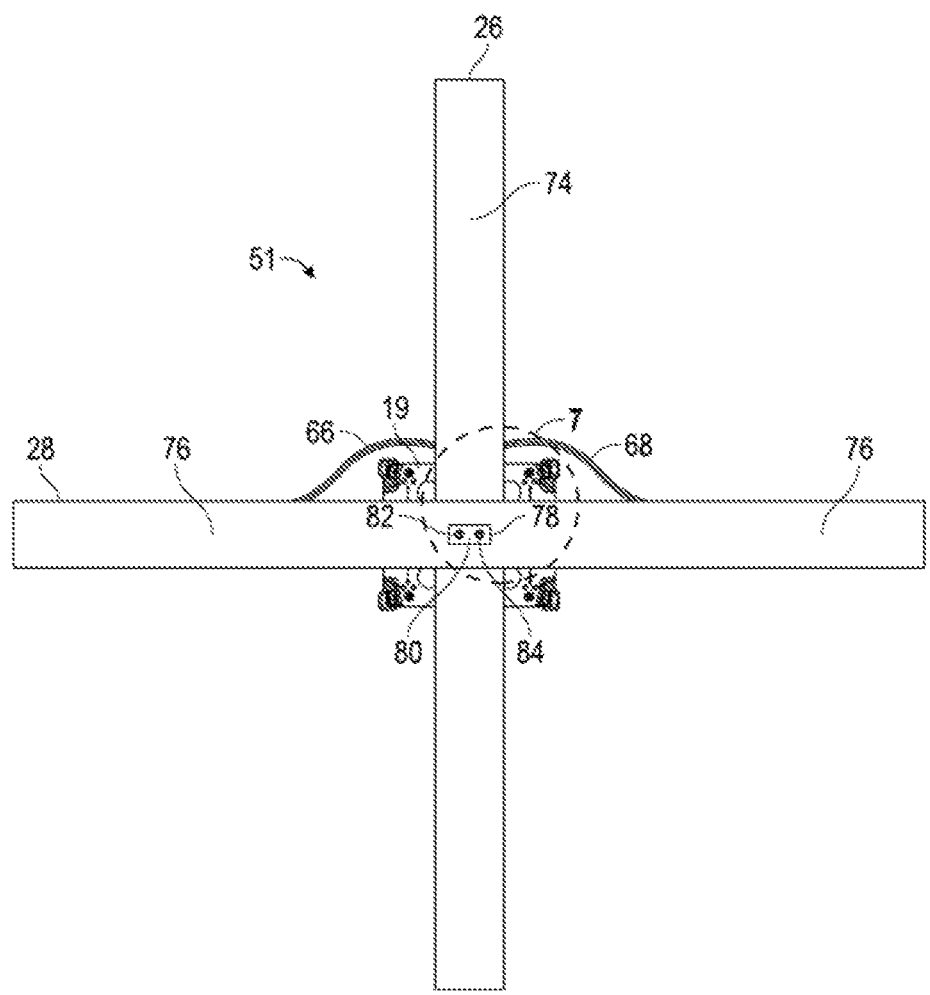
FIG. 6 is a bottom view of the assembly illustrated in FIG. 4.
Figure 7:
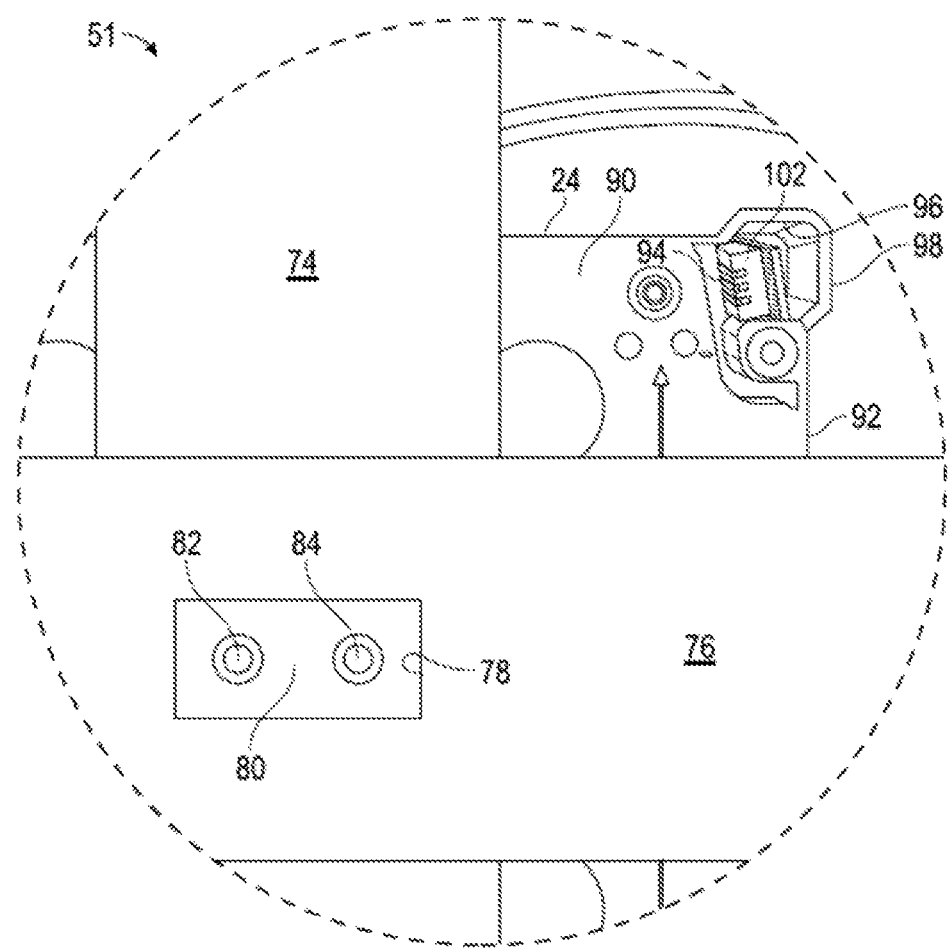
FIG. 7 is a detailed bottom view taken from the callout section appearing in FIG. 6.

Referring to FIGS. 6 and 7, a bottom view of local module assembly 51 shows cross-member 26 having a bottom surface 74, and cross-member 28 having a bottom surface 76. A notch can be formed into bottom surface 74 so that cross-member 28 fits within cross-member 26 as in a tongue-and-groove connection, such that bottom surfaces 74,76 are flush with one another. Additionally, a window 78 is formed by cutting an opening into bottom surface 76, which can extend through the thickness of cross-member 28. Window 78 accommodates a level sensor 80. In one aspect of the present disclosure, level sensor 80 is an ultrasonic ranging module having a sonic transmitter 82 and a sonic receiver 84, commercially available under Model No. HC-SR04, which can provide a ranging accuracy to 3 mm to determine a distance. In this form, level sensor 80 emits eight 4 kHz ultrasonic pulses from sonic transmitter 82 and detects whether a return pulse signal has been reflected back to the sonic receiver 84 from a given surface, to detect a distance between the sensor 80 and that given surface. If a return pulse signal is detected, sensor 80 measures the time from the sending of the ultrasonic pulse at the sonic transmitter 82 to receipt of a reflected pulse at the sonic receiver 84. To determine distance, the measured time is multiplied by the speed of sound (340 m/s), and that product is divided by two. It is contemplated that level sensor 80 could take other forms, such as a time-of-flight sensor (using infrared light to determine distance) or a LADAR sensor (using laser light to determine distance).

FIG. 7 also shows that the local module housing 24 has a bottom panel 90 having an outer edge 92 and a reduced portion 94 receding inwardly from outer edge 92, forming an opening 96 at a corner portion 98 of the housing 24. A local temperature-and-humidity sensor 102 is exposed by the opening 96 to enable the reading of atmospheric temperature and humidity at the container 30, when the assembly 51 is positioned as shown in FIG. 4. Local temperature-and-humidity sensor 102 can be a sensor commercially available from D-Robotics UK under Model No. DHT-11, which has many libraries available for quick programming and which is compatible with commonly-available programmable microcontrollers.

Figure 5:
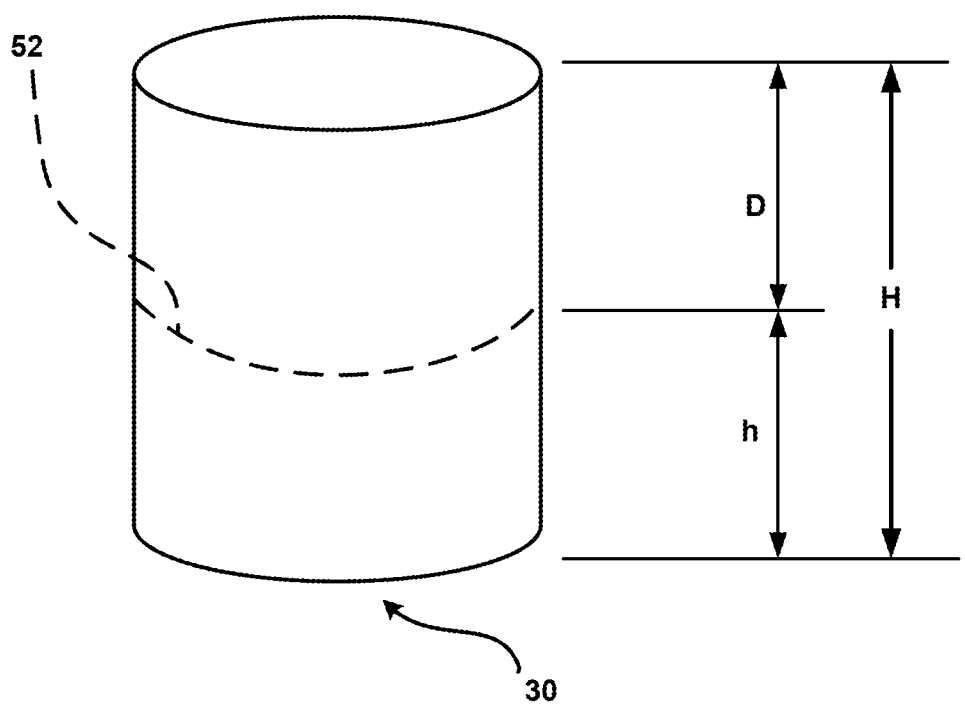
FIG. 5 is a perspective view of a partially-filled container illustrating dimensions associated with the determination of feed level within a container, including the dimension "D" detectable by a level sensor of the local module illustrated in FIG. 4.

Referring to FIGS. 4 and 5, when the local module assembly 51 is oriented as shown in FIG. 4, the sonic transmitter 82 and sonic receiver 84 of level sensor 80 (FIGS. 6 and 7) face a top feed surface 35 of the liquid feed 52 in the container 30. When level sensor 80 is prompted to take a reading (in manner to be described), level sensor 80 emits ultrasonic pulses 86, which bounce off of top feed surface 35 and are detected as returned pulses 88. Level sensor 80 is thereby able to determine the distance "D" illustrated in FIG. 5, in the manner discussed above with regard to FIGS. 6 and 7. The value reported by the level sensor 80 is expressed in terms of a percent of the overall height H of the container 30. Alternatively, the height "h" could be expressed in the reading directly as the measured percent times the overall height H.

Figure 8:
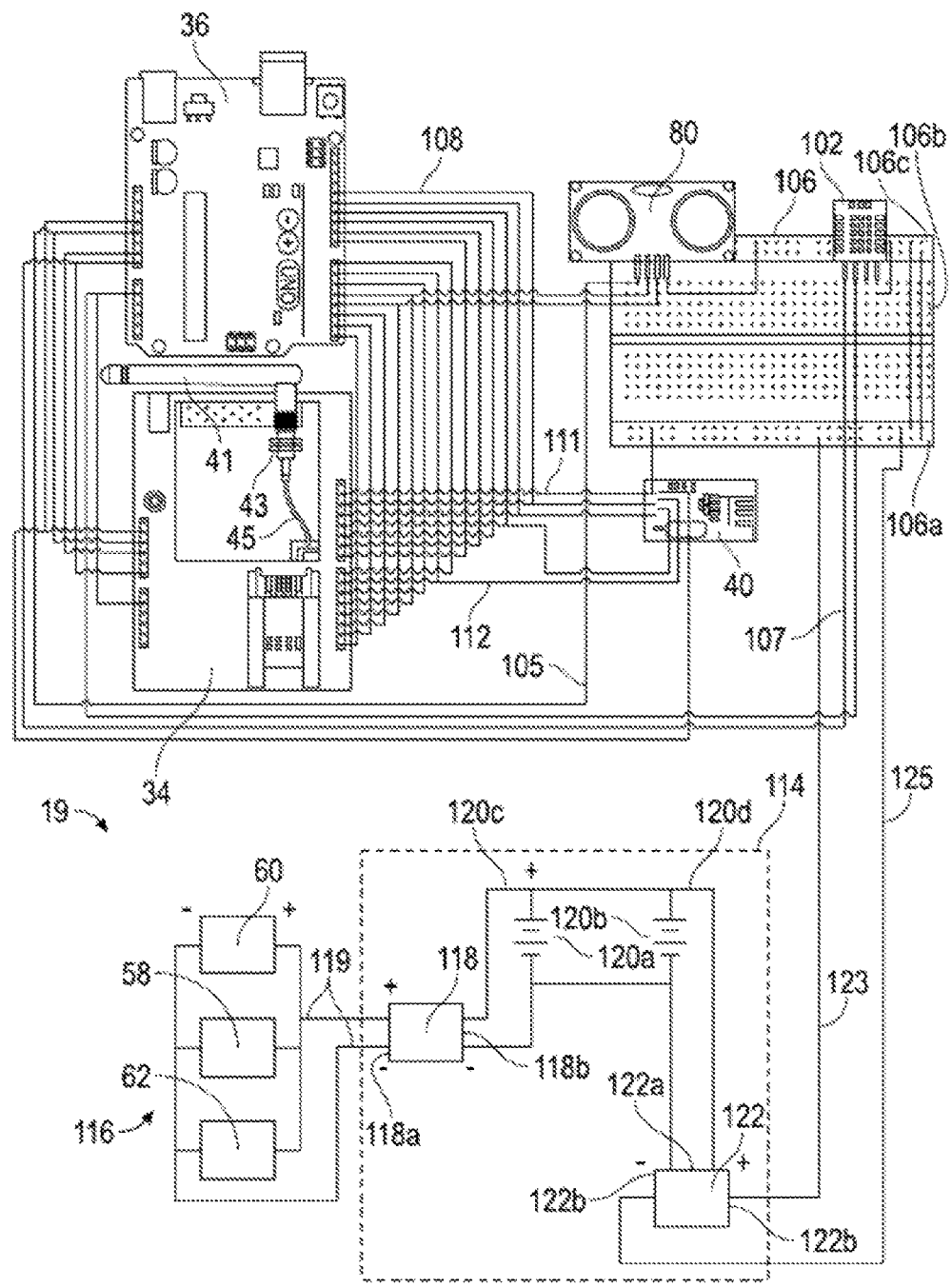
FIG. 8 is a schematic illustration showing connected components of a master module.

FIG. 8 is a schematic diagram illustrating the connections of the devices that together comprise a master module, such as local module 19. A programmable local microcontroller 36 is provided, and in one aspect of the current disclosure can be an Arduino Uno® microcontroller, though other microcontrollers may be suitable for other designs of system 100, and the disclosure is a particular type or brand of microcontroller is not to be considered limiting. Level sensor 80 is electrically coupled to the local microcontroller 36, via wired connections such as at 105, the sensor 80 shown positioned on a commercially-available breadboard 106 having shared power and ground along columns of holes at power strips 106a,b, with central portions such as 106c sharing power and ground along rows of holes. Through the breadboard 106 and wired connections such as at 107, the local temperature-and-humidity sensor 102, described above with regard to FIG. 7, is also electrically coupled to the local microcontroller 36. The communication unit 40 is shown electrically coupled to the local microcontroller 36 via wires such as at 108. In one aspect of the present disclosure, communication unit 40 a cellular modem commercially available from SIMCom Wireless Solutions (in China) under the name "Sim900." The Sim900 modem is suitable for 2G networks supported in the United States by AT&T and T-Mobile Corporation, and such a card allows data transmission utilizing both GSM (global system for mobile communications) and GPRS (general radio packet service) technologies. Cellular modem (communication unit) 34 comprises an antenna 41 connected by a coupling 43 to a lead 45 connecting to internal circuitry of the cellular modem 34, thus allowing the cellular modem 34 to communicate data wirelessly to a user, as previously described with regard to FIG. 3. The Sim900 modem is advantageous for its compatibility with Arduino Uno® microcontrollers, as well as its low cost and easily programmable platform. However, it is contemplated that other modems could be used, especially if it is desired to communicate over 3G or 4G networks; the local module 19 would be compatible with such modems as well.

If it is desired for the local module 19 to communicate with a remote module, the local module can be further provided with a local radio 40 which, in one aspect of the present disclosure, can be commercially available from Nordic Semiconductor under Model No. nRF24. Such a radio, used for both modules 19, 20, is a transceiver and is advantageous for its ability to interface with a programmable microcontroller, as well as for its reliability and effective range (approximately 300 yards). Local radio 40 is shown electrically coupled both to the local microcontroller 36 via wires such as shared wire 108 and to the cellular modem 34 via wires such as at 112.

Also shown in FIG. 8, in one embodiment of the current disclosure, the local module 19 can further comprise a renewable power unit 114 electrically coupled to the local microcontroller 36 and to the solar panels 58,60,62. The solar panels 58,60,62 are connected in parallel to one another, forming an arrangement 116 configured to produce a current output of approximately one ampere (range of 0.95-0.99 mA in sunlight), and a voltage output of 6 V. The renewable power unit 114 comprises a trickle charger 118 having a charger input 118a and a charger output 118b. In one embodiment of the current disclosure, trickle charger can be a 5-volt charger commercially available under Model No. TP4056. The charger input 118a is connected to solar panels 58,60,62 via wiring 119. The renewable power unit 114 further comprises a renewable power source which can comprise a pair of renewable lithium-ion batteries 120a,b, having a source input 120c and a source output 120d. The source input 120c is connected to the charger output 118b. The renewable power unit 114 also comprises a dc-to-dc converter 122 having a converter input 123 and a converter output 122b, which is used to convert the 3.7 V output from the lithium-ion batteries 120a,b to 5V needed to power the local microcontroller 36 and the cellular modem 34. The converter input 123 is connected to the source output 122d, and the converter output 122b connected via power wire 123 to power strip 106a of the breadboard 106, and via ground wire 125 to power strip 106b of breadboard 106. Given the connections shown between the breadboard 106, and the connected components and wiring shown in FIG. 5, the local microcontroller 36 and cellular modem 34 are together powered by the renewable power unit 114 and the solar panels 58,60,62.

Figure 9:
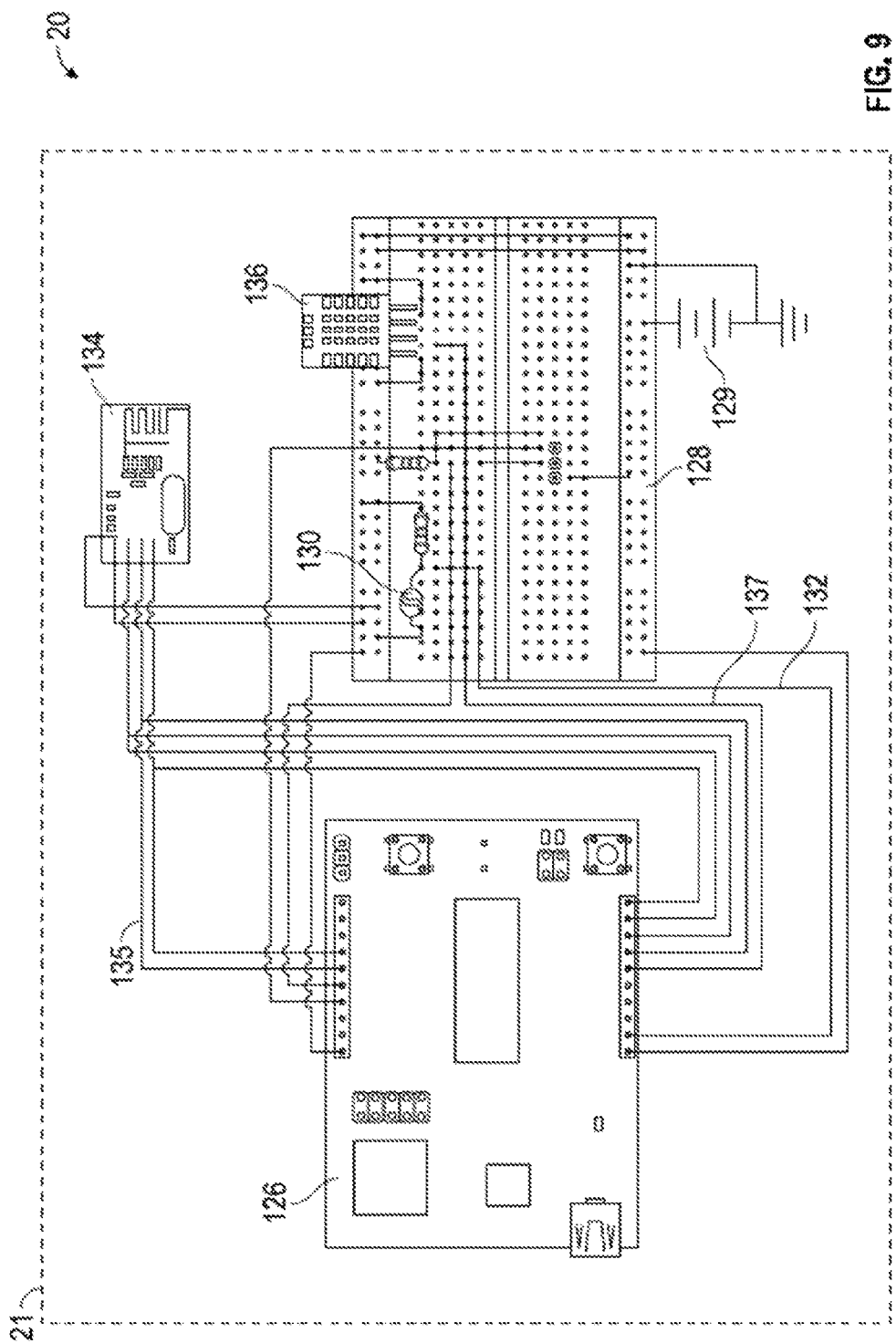
FIG. 9 is a schematic illustration showing connected components of a slave module.

FIG. 9 is a schematic diagram illustrating the connections of the devices that together comprise a slave module, such as remote module 20. A programmable remote microcontroller 126 is provided, and in one aspect of the current disclosure can be a microcontroller commercially available from Texas Instruments, under Model No. MSP430. Local microcontroller 126 is shown having connections to various components via a breadboard 128, functionally identical to breadboard 106 (FIG. 5). Breadboard 128 is connected to a power source 129, which in one embodiment of the present disclosure, can comprise two AAA batteries, with a typical capacity of 1.1 amp hours. A light sensor 130 is electrically coupled to the remote microcontroller 126 via wiring such as at 132. In one embodiment of the present disclosure, light sensor 130 is a photoresistor commercially available from Senba Optical & Electric Company (in China) under Model No. GL5549. Since the level of light to be measured inside a hive does not require a high degree of accuracy (since one only needs to know whether a hive interior has remained dark), a photoresistor such as the GL5549 model is ideally suited to operate in a remote module constructed according to embodiments of the present disclosure. The slave (remote) module 20 further comprises a remote radio 134 electrically coupled to the remote microcontroller 126 via wiring such as at 135. The remote radio 134 is configured to communicate with the local radio 40 (FIGS. 3 and 8) and, in one aspect of the present disclosure, remote radio 134 specifically functions as a transmitter of communications to local radio 40. Ideally the two radios 110, 134 are of the same make and model, though this is not required. The remote module 20 can further comprise a remote temperature-and-humidity sensor 136 electrically coupled to the remote microcontroller 126 via wiring such as at 137. In one embodiment of the present disclosure, sensor 136, like sensor 102 (FIGS. 7 and 8) is available under the DHT-11 designation.

Though FIGS. 8 and 9 illustrate the module components connected with wiring and using breadboards, it is also contemplated that the various module components could instead be connected to one another in a single integrated circuit.

Figure 10A:
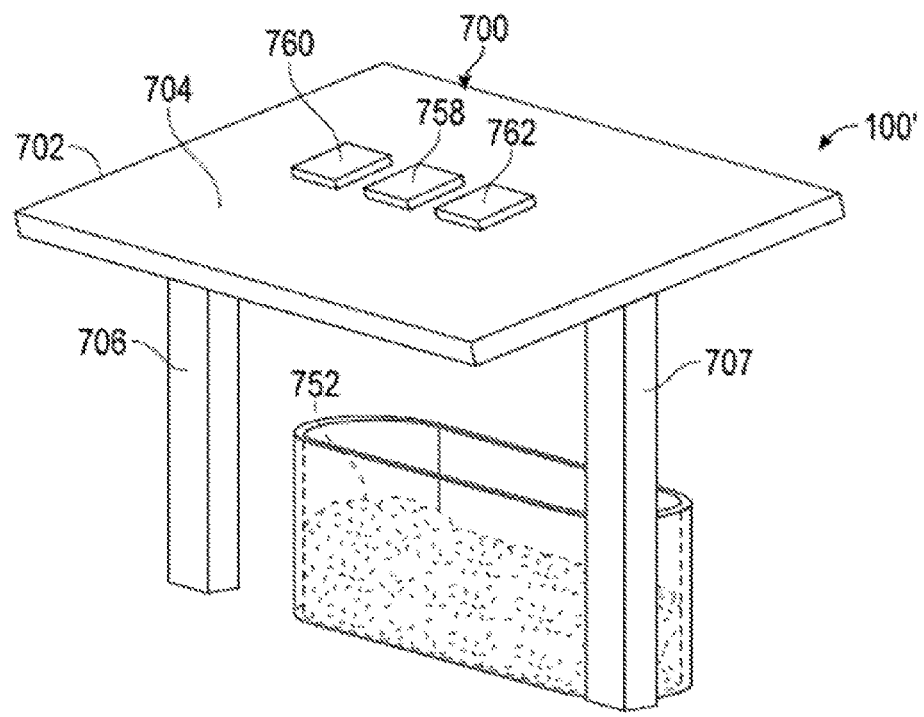
FIGS. 10A and 10B are perspective views showing an exemplary support structure for a master module assembly for detecting the level of solid feed for other animals.
Figure 10B:
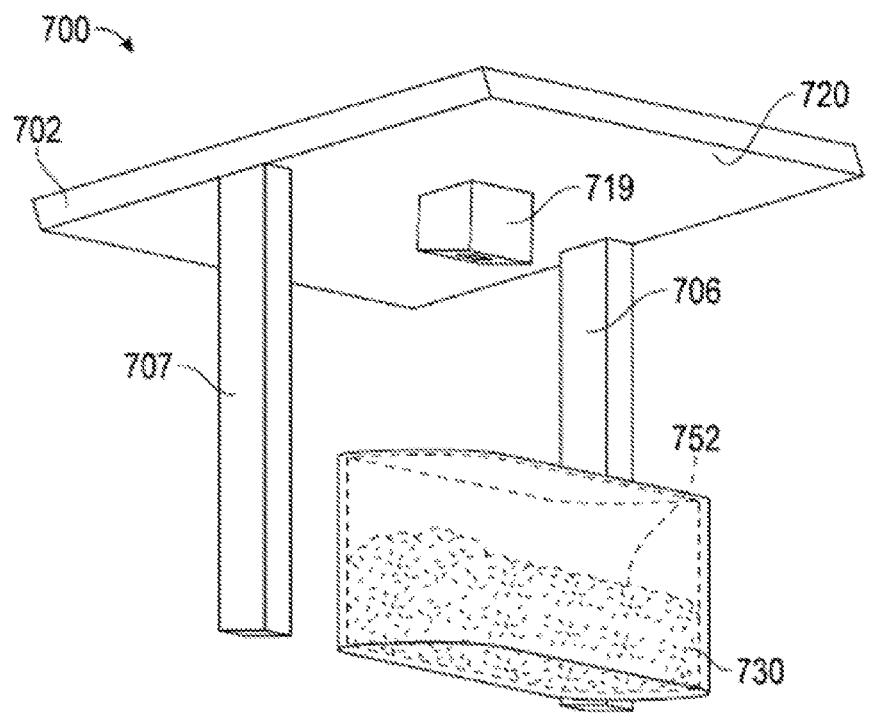

FIGS. 10A and 10B illustrate use of a monitoring system 100' constructed identically, and functioning identically to the feeding system 100 described in the preceding figures, but placed in a solid feed environment. A wide variety of support structures such as at 700 can be used to suspend a local module 719 above a container 730 of solid feed 752. Structure 700 can comprise a roof 702 having a top surface 704 and a bottom surface 720, the roof 702 being supported by legs 706,707. The top surface 704 can have openings in it so as to accommodate one or more solar panels 758,760, 762, functioning to charge a renewable power unit in the local module 719, in the same manner described with regard to FIG. 8. The solid feed remote monitoring system 100' can comprise a remote module (not shown) located at a place where land-based animals congregate, such as a barn, in order to monitor conditions in such locations.

Uses of containers such as at 730, and of solid feed 752, can require differing techniques in how a solid feed level is calculated or otherwise ascertained, in comparison to a liquid level as described above. For example, FIG. 10C schematically illustrates the structure 700 shown in FIGS. 10A and 10B, including the roof 702 and legs 706, 707, with the local module 719 projecting downwardly from the roof 702, and with a level sensor 780 present in local module 719. The level sensor 780 is shown as an ultrasonic ranging module, of the same construction described above for reference character 80 (FIGS. 7-9), though other types of sensors may be used. Container 730, having a top rim 731, is shown positioned on the ground beneath the local module 719 and level sensor 780. The configuration shown in FIG. 10C involves a "blank" distance B, which is the distance from the roof 702 to the container rim 731; a "span" distance S, which may be the height of the container 730; and a distance D', which is measured by the level sensor 780 in the same manner as described for sensor 80 (FIGS. 7-9). In the configuration shown, fill level F can be determined by either of the following formulas, depending on whether F is expressed as an absolute value (such as in inches or meters) or as a percentage:

$$F[\text{abs. value}] = S + B - D', \text{ or}$$

$$F[\%] = (S + B - D)/(S + B).$$

Figure 11A:
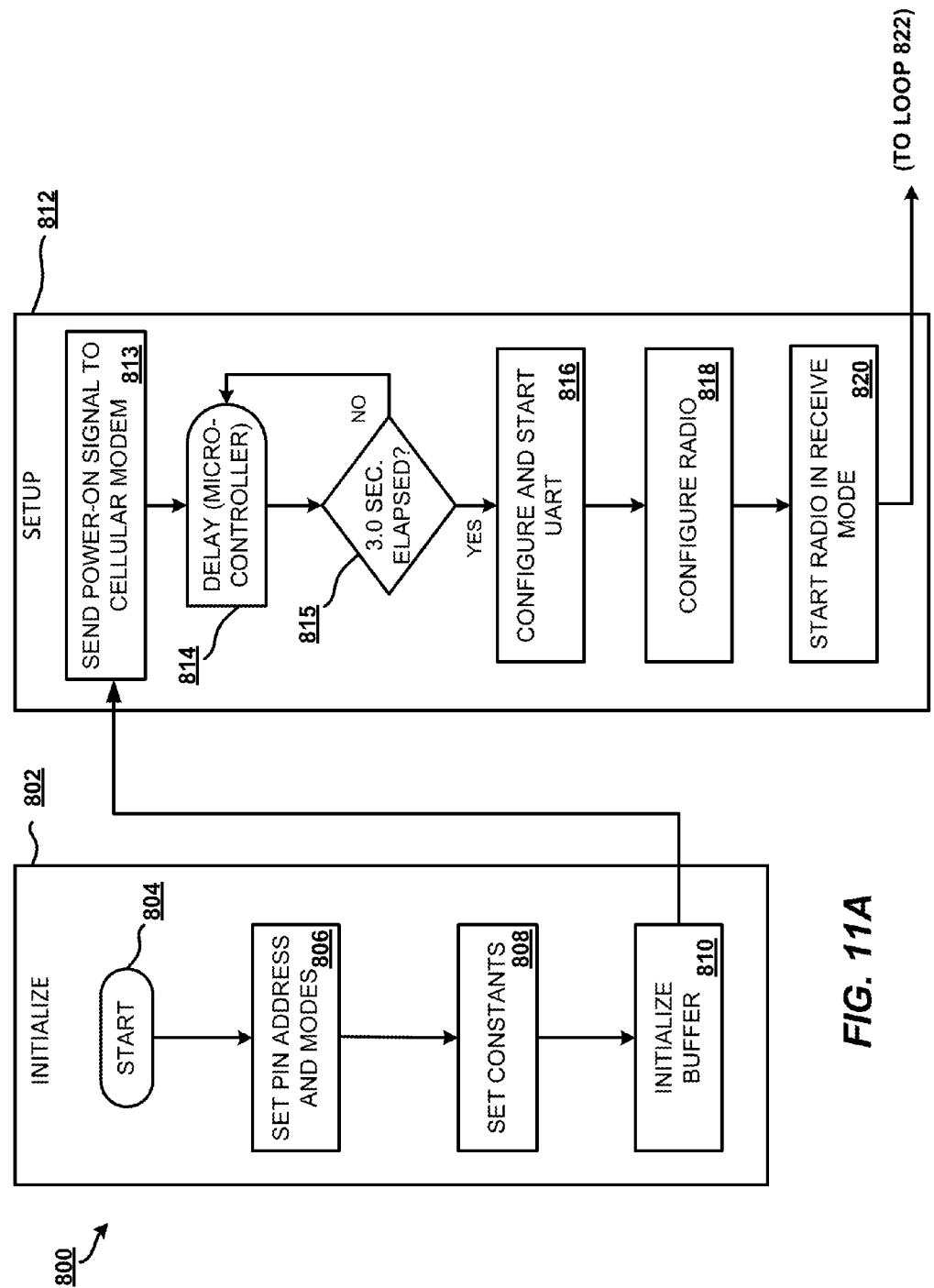
FIGS. 11A and 11B illustrate a flow diagram of an exemplary method to cause a master module to read feed level and, optionally, temperature and humidity at a location local to a feed container, and to then send a text (SMS) communication to a user's electronic communication device containing data regarding the magnitudes of the measured parameters and the locations where each parameter was measured.
Figure 11B:
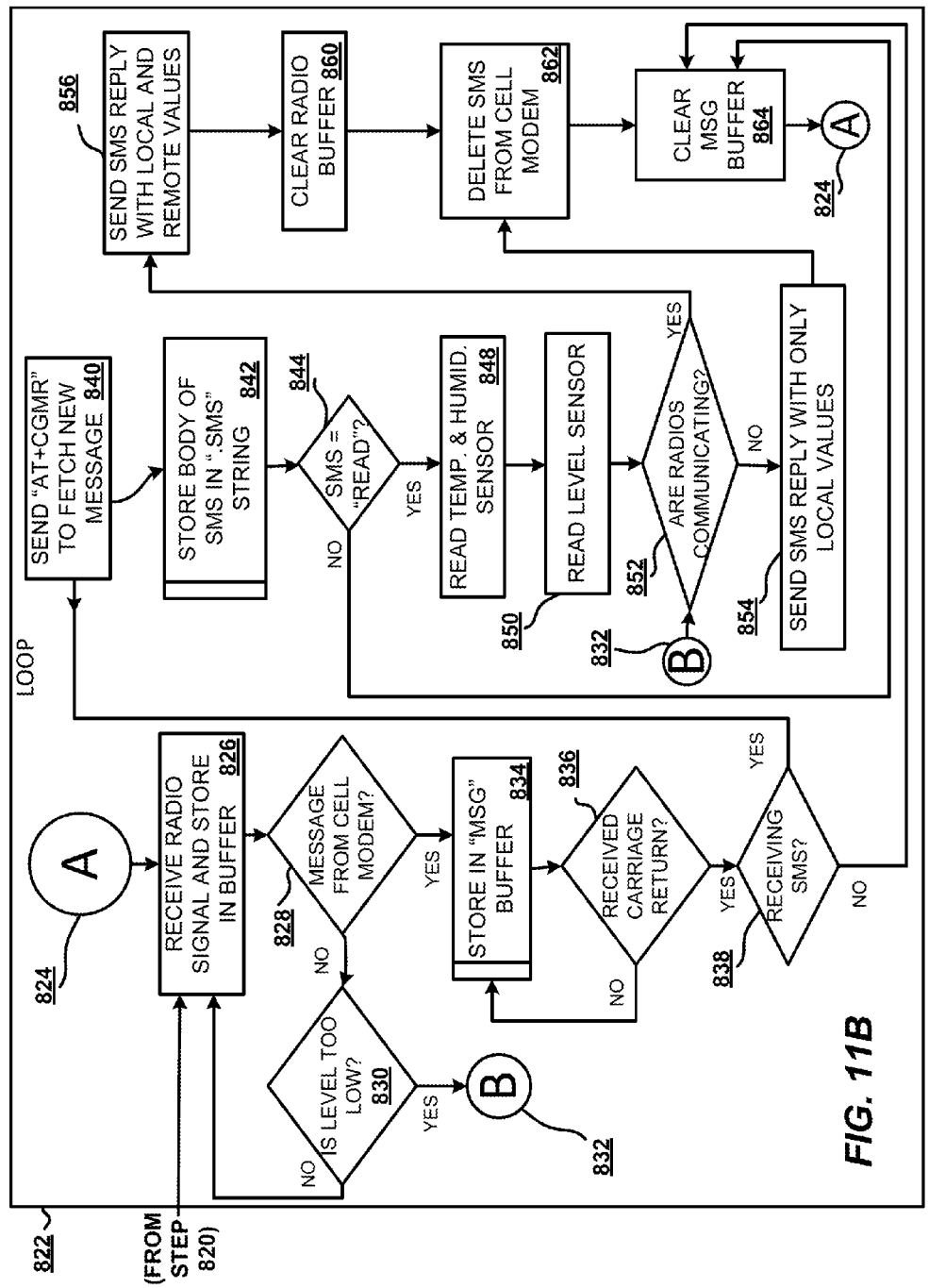

FIGS. 11A and 11B illustrate a flow diagram of a method 800 to cause a master module (here, the local module 19 by way of example) to read feed level and, optionally, temperature and humidity at a location local to the feed container 30 (FIG. 4), and to then send a communication to a user's electronic communication device containing data regarding the magnitudes of the measured parameters and the locations where each parameter was measured. Method 800 comprises steps subdivided into initialization, setup, and loop groups 802, 812, and 822, respectively.

Referring to FIG. 11A, the steps of initialization group 802 are only run once, at the programming stage by the system manufacturer. At block 804, where the method 800 begins, libraries are loaded by the instructions programmed into the local microcontroller 36 (FIGS. 3 and 8). The method 800 continues to block 806, where the pin address and modes are set, meaning that pins of the local microcontroller 36 are assigned to communicate with certain other components of system 100. For example, certain pins of microcontroller 36 can be set as described in below.

| Microcontroller Pins Set | System 100 Device with which Set Microcontroller Pins will Communicate |
|---|---|
| PORTD, pin 7; PORTB, pins 0 & 1 | Cellular modem 34 |
| PORTC, pin 1 | Temperature-and-Humidity Sensor 102 |
| PORTD, pins 5 & 6; PORTB, pins 3, 4, & 5 | Local and Remote radios 110, 134 |

As to an example of a mode setting (in other words, configuring a microcontroller with a library), for either of the temperature-and-humidity sensors 102, 136 (FIGS. 7 and 9, respectively), the mode can be set to "dht11," to reflect the DHT-11 model number of the sensors 102, 136 that can be employed in system 100. The recitation of a particular model of such sensors, however, is not to be considered limiting.

At block 808, constants are set. The steps at block 808 can comprise assigning variables for a radio address, light sensor reading minimum valve, and light sensor reading maximum value. Method 800 then continues to block 810, where the buffer in a memory register of the local microcontroller 36 is initialized. The step at block 810 can comprise assigning a variable for a placeholder, 17 integers long, for placeholder data to send to the local radio 40. However, the placeholder could be as much as 32 bytes, depending on data requirements.

Following the buffer initialization in block 810, method 800 continues to the setup group 812. Like the steps of group 802, the steps of group 812 are only run once, and are performed by the local microcontroller 36. At block 813, the local microcontroller 36 sends a power-on signal to the cellular modem 34 (shown in FIGS. 3 and 8). Then, at block 814, a delay occurs, the purpose of which is to allow the cellular modem 34 to wake up before the microcontroller 36 executes any other tasks. At decision block 815, the microcontroller 36 is instructed to do nothing for a pre-programmed delay period, for example, three seconds. Until that time elapses, the method 800 loops back to the delay block 814, and nothing happens. Upon the elapsing of the delay period (exemplified in block 815 as three seconds), the method 800 continues to block 816. Next, at block 816, the universal asynchronous receiver/transmitter ("UART") microchip in the local microcontroller 36 is configured and started, which enables the serial port and sets the baud rate, for example, to 19200 bps. Method 800 then continues to block 818 of setup group 812, in which the local radio 40 is configured. Programmed configuration instructions instruct the local microcontroller 36 to communicate with the local radio 40 (FIG. 5) over the SPI interface, set radio speed and frequency, and activate the cyclic redundancy check (CRC). Upon configuration of the local radio 40, the method 800 continues to block 820, in which the local radio 40 begins to operate in receive mode. In that mode, the local radio 40 is set to receive signals from a remote radio (such as the remote radio 134 in FIG. 6).

Referring to FIG. 11B, method 800 continues to loop group 822. An encircled symbol "A" 824 serves as a loop marker denoting the start of the loop group 822, and serves as a reference point to indicate when the steps in loop group 822 will repeat. The first step in loop group 822 is at block 826, where the local radio 40, which was set to operate in receive mode (block 820, FIG. 11A), receives a signal from the remote radio 134, and stores that signal in a buffer within the memory of the local microcontroller 36. Additionally, the local microcontroller 36 not only receives the signal from the remote radio 134 via its own radio 110, it also receives any signals sent by the cellular modem 34 (FIG. 8). At block 828, the local microcontroller 36 queries whether a signal has been received from the cellular modem 34. Absent such a signal, the method 800 goes to decision block 830, where the microcontroller 36 prompts the level sensor 80 (FIGS. 4-7) to sense the level of feed within the container 30 (FIGS. 2 & 3). The local microcontroller then compares the feed level data received from the level sensor 80 to a predetermined threshold level, which may be stored in a memory of the local microcontroller 36 during programming or initiation steps. In one aspect of the current disclosure, the threshold level can be "15%," though the system 100 can allow the end user to enter a custom threshold value, or even deactivate level reporting by entering a negative value. Referring again to block 830, if the detected feed level is at or above the predetermined threshold level, the method 800 loops back to block 826. If, however, the detected feed level is below the predetermined threshold level, the method 800 skips to chart location 832, represented by an encircled "B" in FIG. 11B. At that location 832, the method 800 skips to decision block 852, to be explained in sequence. Referring back to decision block 828, if a signal has been received from the cellular modem 34, the method 800 continues to block 834, where the microcontroller 36 starts to read the message from the cellular modem 34, one character at a time, and sequentially stores each read character in a buffer designated as "MSG" by coding. Next, method 800 continues to a decision block 836, where execution of steps depends on whether a carriage return has been received from the cellular modem 34. At block 836, the microcontroller 36 evaluates the buffer to determine whether a carriage return character has been stored. If not, the method 800 loops back to block 834, and characters continue to be stored in the buffer as they are received from the cellular modem 34. If, however, the microcontroller 36 detects that a carriage return is present in the buffer, then the microcontroller 36 retains the number of characters present in the buffer immediately prior to receiving the carriage return, and the method 800 continues to decision block 838. At decision block 838, the local microcontroller 36 detects whether the signal being received is, in fact, a text message (SMS) or, instead, whether the signal received is something else, such as a phone call. A message is only confirmed as an SMS message if the cellular modem 34 outputs "+CMTI," which is a standard code word that cellular modems can use to notify a computer that an SMS message has been received, and to specify to the computer the memory location where the SMS message was stored. If no SMS message was received, the method 800 skips to block 864, where the MSG buffer is cleared, and the method reaches the looping marker 824, thus causing the method 800 to return to block 826, the first block in loop group 822. If, however, a valid SMS message was received, method 800 continues sequentially to block 840.

At block 840, the local microcontroller 36 sends a command, which can be the command "AT+CGMR," for the cellular modem 34 to communicate, to the microcontroller 36, the contents of the SMS message that the cellular modem 34 received in block 828. Method 800 then proceeds to block 842, where the body of the received SMS message (i.e., just the contents of the SMS message, without associated metadata like sender, date, etc.) is stored in a buffer other than that used at blocks 824 and 834. Next, at block 844, the buffer referenced in block 842 is checked to determine whether the SMS message stored therein is a valid command or, instead, something else (such as a wrong number or a cell provider sending a text about a user's bill status). As an example, the local microcontroller 36 can be programmed to recognize only the character string "READ" as a valid command, though the programming instructions could specify some other character string to serve as the valid command. The "yes" line from block 844 means that a valid command has just been received, and the method 800 proceeds to block 848. If, however, the stored SMS message is not a valid command, then method 800 goes to block 864 described above, where the MSG buffer is cleared.

At block 848, the local microcontroller 36 reads a temperature-and-humidity sensor, such as sensor 102, described with regard to FIGS. 7 and 8, and returns temperature and humidity values. The humidity value is expressed as a percentage. In one aspect, the temperature value can be expressed in degrees Fahrenheit, but in another aspect, the reported temperature can be expressed in degrees Celsius, if programming instructions so indicate. Method 800 then proceeds to block 850, where the microcontroller 36 reads the level of the feed in container 30 (FIGS. 2 & 3), such as by receiving information from level sensor 80, described with regard to FIG. 5. Next, method 800 advances to decision block 852, in which the local microcontroller 36 assesses whether the local radio 40 and the remote radio 134 are communicating with one another, in which event data from both radios would be stored in the microcontroller 36. If such radio communication is present, then the method 800 proceeds to block 856, where method 800 causes an SMS reply message to be sent to the sender of the SMS message in block 838, the reply message containing not only readings received from the sensors in the local module 19 (the "local values"), but also readings from sensors of the remote module 20 (the "remote values"). After the sending of that SMS reply message in block 856, the method 800 proceeds to block 860, where the SMS reply text is cleared from the microcontroller buffer (identified as "radio buffer" in block 860), that is holding data from both radios 110, 134. Following the clearing of the radio buffer in block 860, method 800 advances to block 862, where the microcontroller 36 sends a command to the cellular modem 34 to delete its SMS messages, as they are no longer needed at this stage of method 800. Next, at block 864, the MSG buffer is cleared of variables and data from the sensor readings, preparing it for storage of new data. From block 864, the method 800 loops back to the first loop step, i.e., block 826, the looping point denoted by the looping marker 824, Referring back to block 852, if the local radio 40 and the remote radio 134 are not communicating with one another, the method 800 proceeds to block 854, where the method 800 causes an SMS reply message to be sent to the sender of the SMS communication of block 838, the message containing information reporting only the local values. From block 854, the method 800 skips to block 862, and then to block 864 and to the looping marker 824, with blocks 862 and 864, as well as the looping marker 824, described above.

Figure 12A:
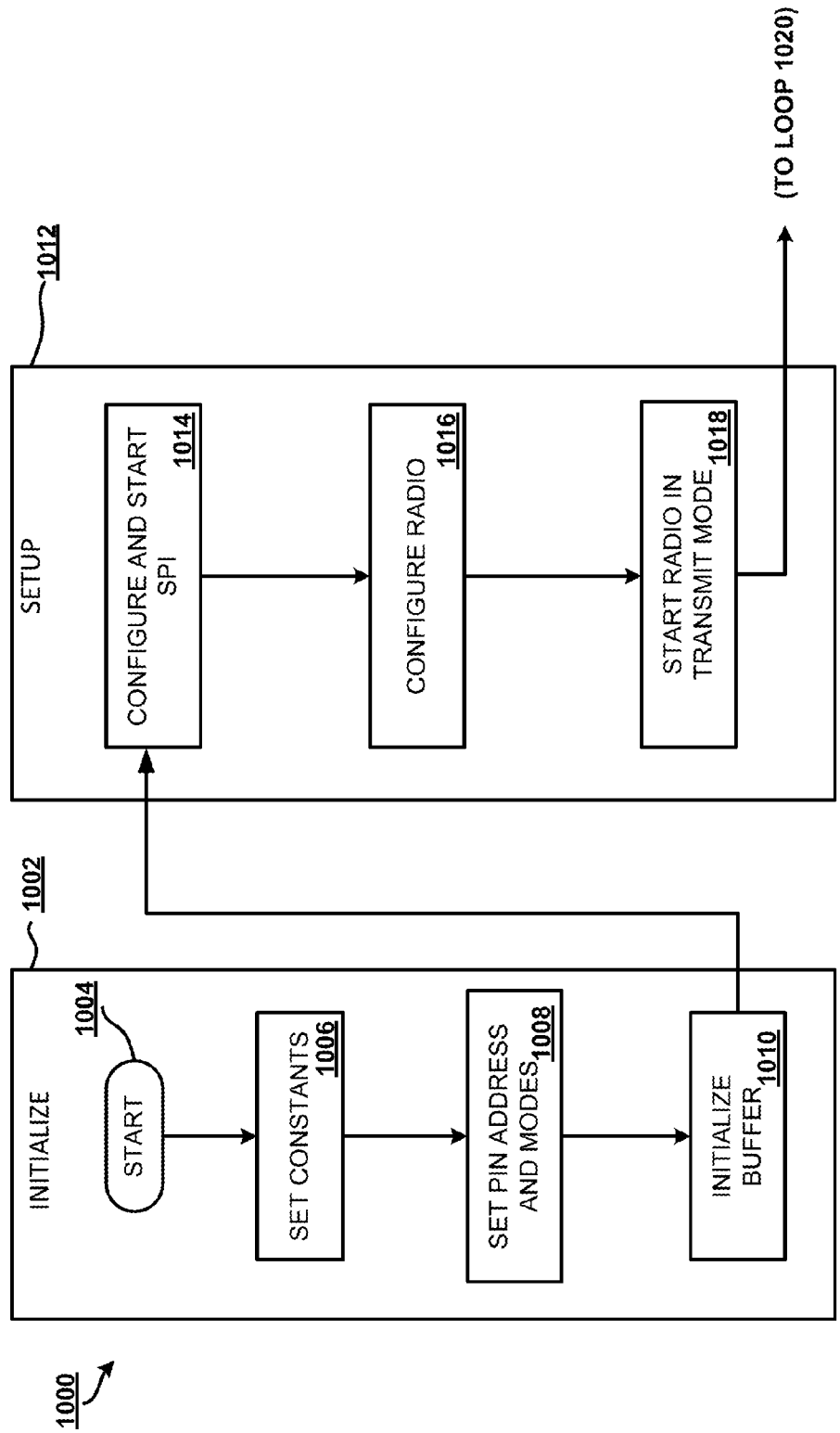
FIGS. 12A and 12B illustrate a flow diagram of an exemplary method to cause a slave module to read data from sensors measuring temperature, humidity, and light level at a location remote from the local module, and to transmit that data via an onboard radio to another radio located at the local module.
Figure 12B:
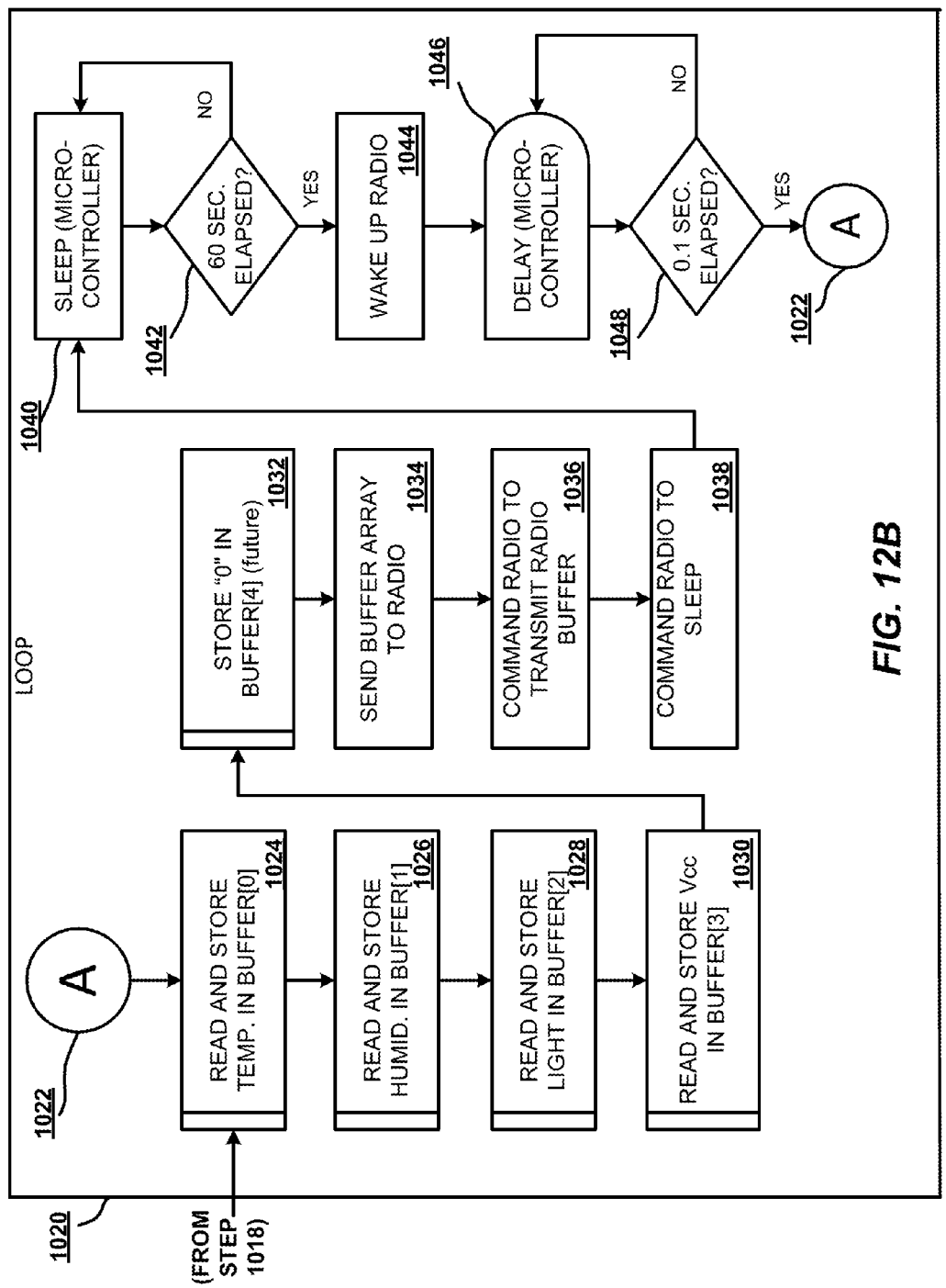

FIGS. 12A and 12B illustrate a flow diagram of a method 1000 to cause a slave module (here, the remote module 20 by way of example) to read data from sensors measuring temperature, humidity, and light level at a location remote from the local module 19, and to transmit that data from the remote radio 134 (FIG. 9) to the local radio 40 in local module 19 (FIGS. 3 and 8). Method 1000 comprises steps subdivided into initialization, setup, and loop groups 1002, 1012, and 1022, respectively.

Referring to FIG. 12A, and to initialization group 1002, at block 1004 the method 1000 begins. At block 1004, certain libraries, or subprograms, stored in the remote microcontroller 126 (shown in FIG. 9) can be loaded into instructions programmed into the remote microcontroller 126, such as libraries for the remote radio 134 (FIG. 9), for generation of strings, and for the SPI. From block 1004, the method 1000 continues to block 1006. At block 1006, constants are set. The steps at block 1006 can comprise assigning variables for the remote radio address, light sensor reading minimum valve, and light sensor reading maximum value. At block 1008, the pin address and modes are set. In other words, certain microcontroller pins are assigned to the programming instructions. For example, Port 2, pins 0, 1, and 2 can be set for communication between the microcontroller 126 and remote radio 134; and Port 1, pin 4 can be set for the microcontroller 126 to communicate with the temperature-and-humidity sensor 136 (FIG. 9). From block 1008, method 1000 proceeds to block 1010, where a buffer in a memory register of the microcontroller 126 is initialized. The step at block 1010 can comprise assigning a variable for a placeholder, five integers long, for placeholder data to send to the remote radio 134. However, the placeholder could be as much as 32 or even more bytes, depending on data requirements.

From block 1010, method 1000 proceeds to the setup group 1012 of steps, which are all performed by the local microcontroller 126. At block 1014, the SPI is configured and started, such that the SPI mode is configured, SPI communication then also begins at block 1014. Next, at block 1016, the remote radio 134 (FIG. 9) is configured. This can comprise commanding the local microcontroller 126 to communicate over the SPI interface with the remote radio 134, set radio speed and frequency, and activate the CRC. The method 1000 then proceeds to block 1018, where the remote radio 134 is started in transmit mode. In that mode, the remote radio 134 is set to transmit signals to the local radio 40 (FIGS. 3 and 8). From block 1018, the method 1000 enters the loop group 1020 of steps (FIG. 12B).

Referring to FIG. 12B, the method 1000 proceeds from block 1018 (FIG. 12A) to loop group 1020. An encircled symbol "A" 1022 denotes a loop marker indicating the start of the loop group 1022, thus indicating when the steps in loop group 1022 will repeat. Buffer storage steps referenced in loop group 1020 refer to storage of information in a buffer located in the memory of remote microcontroller 126 of the remote module 20 (FIG. 9). The first step in loop group 1022 is at block 1024, where the temperature is read from the temperature-humidity sensor 136 (FIG. 9), and the returned value is stored in "buffer[0]." In one aspect, the value can be expressed in degrees Fahrenheit, but in another aspect, the reported temperature can be expressed in degrees Celsius, if programming instructions so indicate. From block 1024, the method 1000 advances to block 1026, where humidity is read from the temperature-and-humidity sensor 136, expressed as a percentage, and stored into "buffer[1]." Method 1000 then proceeds to block 1028, where the light is read from the photoresistor 130 (shown in FIG. 6). Based on the intensity detected from the photoresistor 130, the remote microcontroller 126 assigns a value to be stored into "buffer[2]," which can be "0" for dark, "1" for dim, "2" for medium, or "3" for bright. Such readings will enable a user to determine whether an event, such as the knocking over of a beehive 10 (FIGS. 1 and 2) has occurred. In one aspect of the present disclosure, programmed instructions can link each returned value to a different text message to be sent to the user. For instance, a value of "1" present in the buffer array transmitted to the local radio 40 can cause the local microcontroller 36 to compose the character strings "the light is dim," as well as "in the hive," in the SMS reply message sent by the local microcontroller 36 in FIG. 11B, block 856. Next, at block 1030, the microcontroller 126 reads the millivolts of the remote module batteries 129 (FIG. 9), and stores that value into "buffer[3]." The method 1000 proceeds to block 1032, where a zero value is stored in "buffer[4]." In other aspects of the invention, however, other parameter readings can be stored into the buffer, such as microcontroller temperature.

Still referring to FIG. 12B, with the buffers [0]-[4] now all having values stored therein, a buffer array exists. At block 1034, the buffer array is sent from the remote microcontroller 126 to a buffer in the remote radio 134 (FIG. 9), and this transmission occurs over the SPI interface. The method 1000 proceeds to block 1036, in which the remote microcontroller 126 is instructed to direct the remote radio 134, over the SPI interface, to transmit its data over the air. Next, at block 1038, programming instructions instruct the microcontroller 126 to send a command, over the SPI interface, for the remote radio 134 to go into a deep sleep mode. The method 1000 proceeds to block 360, in which the microcontroller 126, itself, is directed to go into a deep sleep mode. The deep sleep modes induced at blocks 1038 and 360 promote conservation of battery power. Next, at decision block 362, the duration of the sleep of the microcontroller 126 can be set at sixty seconds, though other programmed durations can also be implemented. At block 362, if sixty seconds have not yet elapsed, the microcontroller 126 remains in its sleep state. Upon the elapsing of sixty seconds, however, the microcontroller 126 is woken at block 364, where it is now in full power mode. Then, at block 366, a delay occurs, the purpose of which is to allow the remote radio 134 (FIG. 9) to wake up before the microcontroller 126 executes any other tasks upon its own awakening. At decision block 366, the microcontroller 126 is instructed to do nothing for 0.1 seconds. Until that time elapses, the method 1000 loops back to the delay block 366, and nothing happens. Upon the elapsing of 0.1 seconds, the method 1000 reaches the loop marker 1022, and the steps in loop group 1020 are repeated, beginning with block 1024.

Figure 13A:
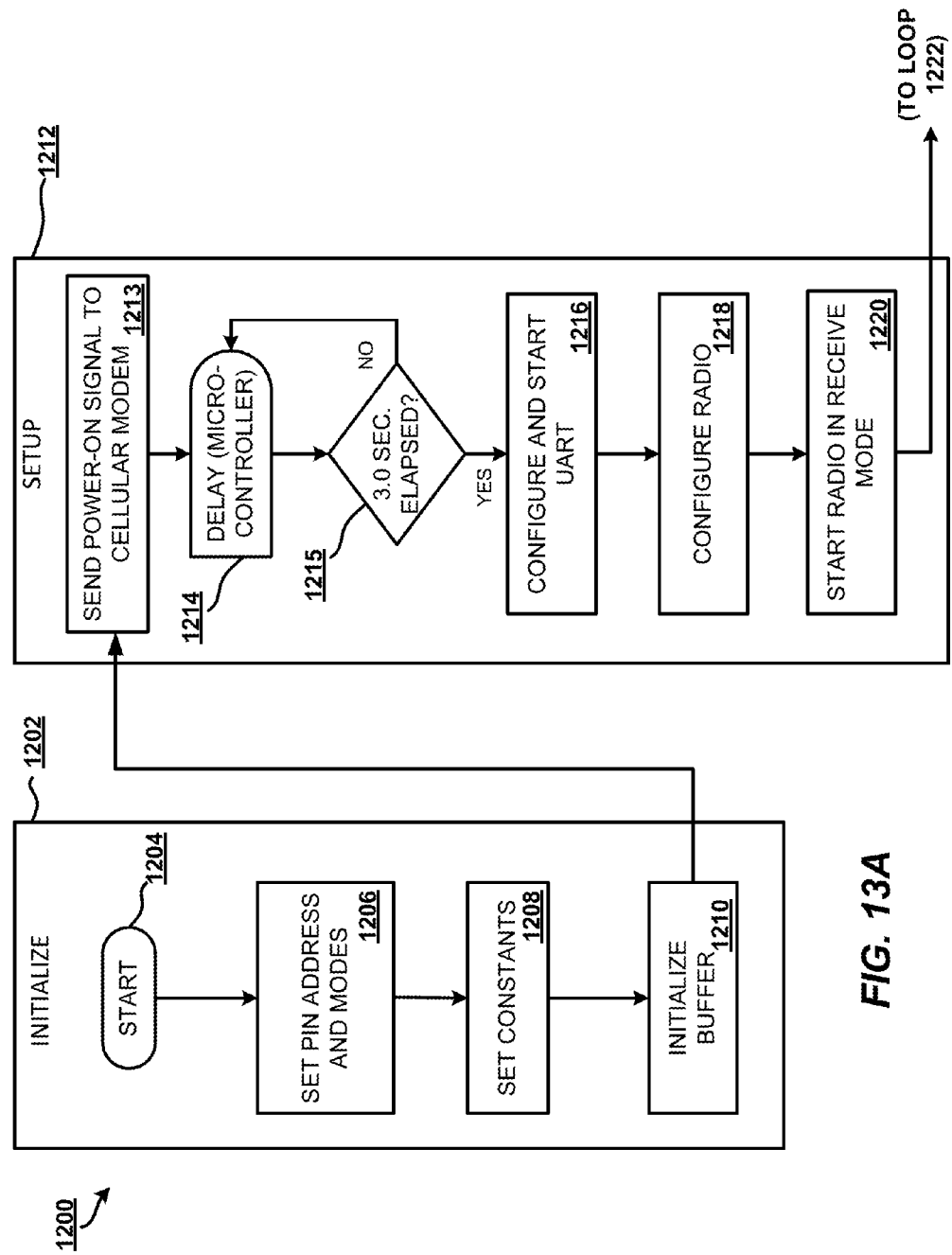
FIGS. 13A and 13B illustrate a flow diagram of exemplary method in which a master module is caused to read feed level and, optionally, temperature and humidity at a location local to a feed container, and to then write data to a database on a server instead of exchanging text messages.
Figure 13B:
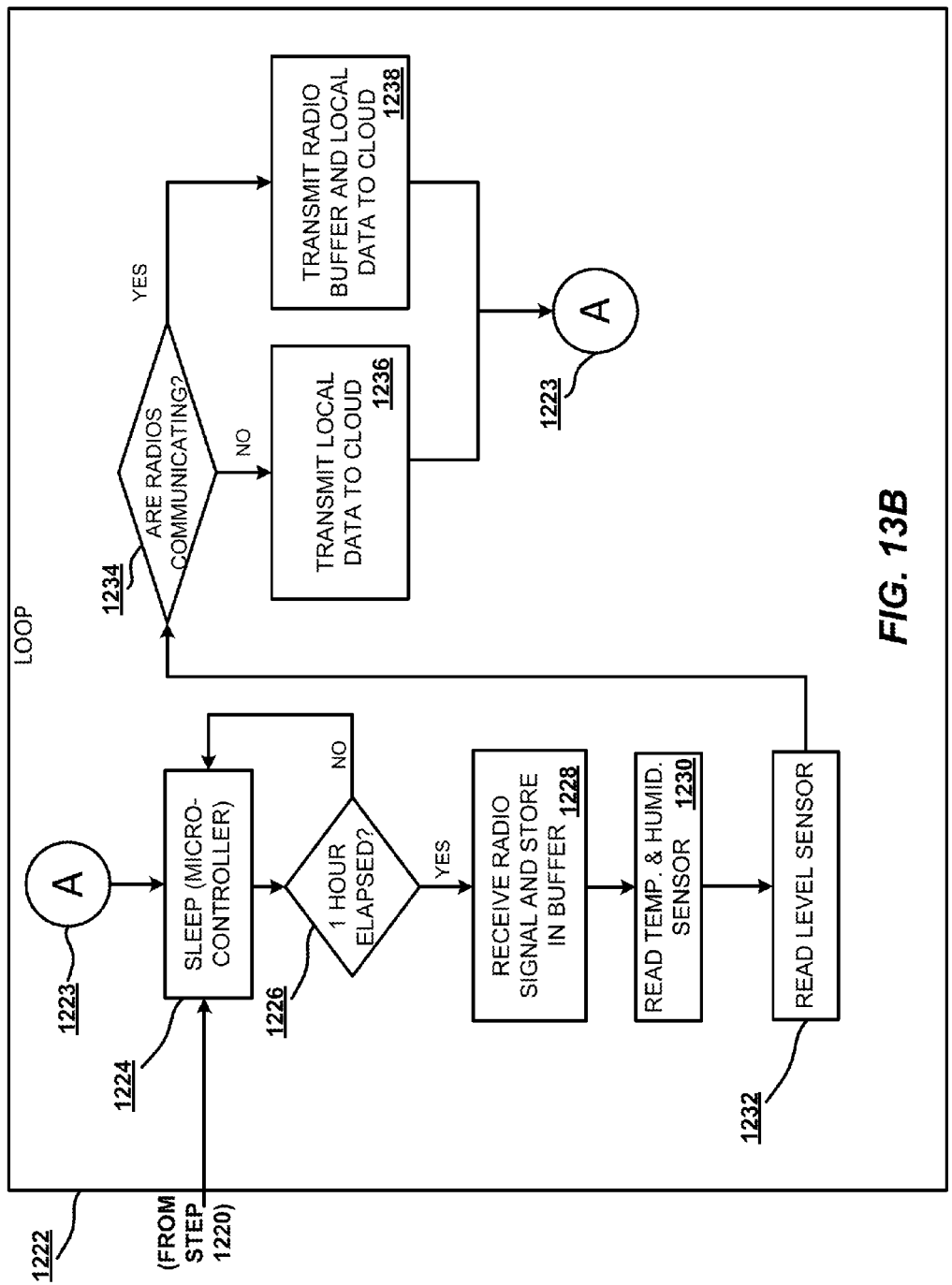

FIGS. 13A and 13B illustrate a flow diagram of alternate method 1200, in which a master module is caused to read feed level and, optionally, temperature and humidity at a location local to a feed container, and to then write data to a database on a server, instead of exchanging text messages (discussed with regard to FIG. 9). Method 1200 comprises steps subdivided into initialization, setup, and loop groups 1202, 1212, and 1222, respectively.

The portion of the flow diagram FIG. 13A involves steps identical to those discussed with regard to FIG. 11A, thus the last two digits in each reference character of FIG. 13A are identical to the last two digits in corresponding reference characters of FIG. 11A. Accordingly, as in method 800 of FIG. 11A, the steps of initialization group 1202 are only run once, at the programming stage by the system manufacturer. At block 1204, where the method 1200 begins, libraries are loaded by the instructions programmed into the local microcontroller 36 (FIGS. 3 and 8). The method 1200 continues to block 1206, where the pin address and modes are set, meaning that pins of the local microcontroller 36 are assigned to communicate with certain other components of system 100. For example, certain pins of microcontroller 36 can be set as described in below.

| Microcontroller Pins Set | System 100 Device with which Set Microcontroller Pins will Communicate |
|---|---|
| PORTD, pin 7; PORTB, pins 0 & 1 | Cellular modem 34 |
| PORTC, pin 1 | Temperature-and-Humidity Sensor 102 |
| PORTD, pins 5 & 6; PORTB, pins 3, 4, & 5 | Local and Remote radios 110, 134 |

As to an example of a mode setting (in other words, configuring a microcontroller with a library), for either of the temperature-and-humidity sensors 102, 136 (FIGS. 7 and 9, respectively), the mode can be set to "dht11," to reflect the DHT-11 model number, described previously, of the particular example of the sensors 102, 136 that can be employed in system 100.

At block 1208, constants are set. The steps at block 1208 can comprise assigning variables for a radio address, light sensor reading minimum valve, and light sensor reading maximum value. Method 1200 then continues to block 1210, where the buffer in a memory register of the local microcontroller 36 is initialized. The step at block 1210 can comprise assigning a variable for a placeholder, 17 integers long, for placeholder data to send to the local radio 40. However, the placeholder could be as much as 32 bytes, depending on data requirements.

Following the buffer initialization in block 1210, method 1200 continues to the setup group 1212. Like the steps of group 1202, the steps of group 1212 are only run once, and are performed by the local microcontroller 36. At block 1213, the local microcontroller 36 sends a power-on signal to the cellular modem 34 (shown in FIG. 5). Then, at block 1214, a delay occurs, the purpose of which is to allow the cellular modem 34 to wake up before the microcontroller 36 executes any other tasks. At decision block 1215, the microcontroller 36 is instructed to do nothing for a pre-programmed delay period, for example, three seconds. Until that time elapses, the method 1200 loops back to the delay block 1214, and nothing happens. Upon the elapsing of the delay period (exemplified in block 1215 as three seconds), the method 1200 continues to block 1216. Next, at block 816, the universal asynchronous receiver/transmitter ("UART") microchip in the local microcontroller 36 is configured and started, which enables the serial port and sets the baud rate, for example, to 19200 bps. Method 1200 then continues to block 1218 of setup group 1212, in which the local radio 40 is configured. Programmed configuration instructions instruct the local microcontroller 36 to communicate with the local radio 40 (FIGS. 3 and 8) over the SPI interface, set radio speed and frequency, and activate the cyclic redundancy check (CRC). Upon configuration of the local radio 40, the method 1200 continues to block 1220, in which the local radio 40 begins to operate in receive mode. In that mode, the local radio 40 is set to receive signals from a remote radio (such as the remote radio 134 in FIG. 9).

Referring to FIG. 13B, the method 1200 progresses to the loop group 1222 of steps, with a loop marker 1223, symbolized by the encircled letter "A," indicates the start of a loop. At block 1224 the microcontroller 126, itself, is directed to go into a deep sleep mode. This deep sleep mode promotes conservation of battery power. Next, at decision block 1226, the duration of the sleep of the microcontroller 126 can be set at sixty minutes, though other programmed durations can also be implemented. At block 1226, if sixty minutes have not yet elapsed, the method 1200 loops back to block 1224, and microcontroller 126 remains in its sleep state. Upon the elapsing of sixty minutes, the method 1200 advances to block 1228, where microcontroller 126 is woken and polls any other radio on the network, reads any available messages from the radios 110, 134, and stores them in a buffer. Next, at block 1230, the temperature and humidity are read from sensor 102 (FIG. 5), and the returned values are stored into a stored variable, expressing temperature in degrees Fahrenheit and humidity as a percent in the coding. Then, at block 1232, the level sensor 80 (FIG. 5) is read, and the value stored into a variable. Method 1200 then advances to decision block 1234, where the microcontroller 36 checks whether the local radio 40 has data stored in the microcontroller 36. If not, then the method 1200 progresses to block 1236, where the microcontroller 36 sends its data, along with the stored radio data, to the cellular modem 34 to be transmitted to a database on a server connected to the internet. The modem 34 uses TCP to connect to the server via a port, typically "80" on the modem and insert the data into the database via a script, such as PHP, residing on the server. Referring back to block 1234, if the local radio 40 does not have data stored in the microcontroller 36, the method goes to block 1238, where the microcontroller 36 sends its data to the cellular modem 34 to be transmitted back to the database on a server connected to the internet. The modem 34 uses TCP in the same manner described with regard to block 1236. From either block 1236 or block 1238, the method 1200 returns to the beginning of the loop, as noted by loop marker 1223.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

The which is claimed is:

1. A remote monitoring system, comprising:
   a local module configured to be suspended above a container having an internal cavity, the local module comprising
   a local microcontroller,
   a feed level sensor electrically coupled to the local microcontroller, the feed level sensor configured to determine a distance between the feed level sensor and a top feed surface of any feed stored in the internal cavity of the container, and
   a communication unit electrically coupled to the local microcontroller, the communication unit being configured to exchange data with the local microcontroller and to wirelessly send data to a communication device of a user; and
   a remote module configured for placement inside a beehive spaced from the local module, the remote module comprising
   a remote microcontroller,
   a light intensity sensor electrically coupled to the remote microcontroller, the light intensity sensor configured to sense light intensity within the beehive, and
   a remote transmitter electrically coupled to the remote microcontroller, the remote transmitter configured to communicate alphanumeric intensity data generated from the light intensity sensed by the light intensity sensor to at least one of the local module and the communication device.

2. The remote monitoring system of claim 1, wherein:
   the remote microcontroller is configured to
   assign an intensity value to the light intensity sensed by the light intensity sensor,
   store the intensity value into a memory of the remote microcontroller, and
   transmit the intensity value to at least one of the local module and the communication device; and
   the local microcontroller is configured to
   receive the intensity value from the remote transmitter via a local transmitter communicating with the local microcontroller,
   compose a character string corresponding to the intensity value, and
   transmit the character string to the communication device of the user.

3. The remote monitoring system of claim 1, wherein the feed level sensor is configured to emit an ultrasonic pulse and to receive a reflected ultrasonic pulse bounced off of the top feed surface, wherein in the feed level sensor is configured to send respective ultrasonic pulse and reflected ultrasonic pulse signals to the local microcontroller, and wherein the local microcontroller determines a distance reading based on the respective ultrasonic pulse and reflected ultrasonic pulse signals.

4. The remote monitoring system of claim 1, wherein the local module further comprises:
   a renewable power unit electrically coupled to the local microcontroller; and
   at least one solar panel electrically coupled to the renewable power unit.

5. The remote monitoring system of claim 4, wherein the renewable power unit comprises:
   a trickle charger, the trickle charger having a charger input and a charger output, the charger input connected to the at least one solar panel;
   a renewable power source having a source input and a source output, the source input connected to the charger output; and
   a dc-to-dc converter having a converter input and a converter output, the converter input connected to the source output, the converter output connected to the local microcontroller.

6. The remote monitoring system of claim 4, wherein the at least one solar panel comprises a plurality of solar panels connected in parallel to one another and configured to produce a current output of approximately one ampere.

7. The remote monitoring system of claim 1, wherein the local module further comprises a local temperature-and-humidity sensor electrically coupled to the local microcontroller.

8. The remote monitoring system of claim 1, wherein the local module further comprises a receiver electrically coupled to the local microcontroller and to the communication unit.

9. The remote monitoring system of claim 1, wherein the light intensity sensor comprises a photoresistor.

10. A method of remotely monitoring a feed environment, comprising:
    generating feed level data from a sensed level of feed stored within a container;
    transmitting feed level data over a first communication link to a communication device of a user;
    sensing light intensity in a beehive spaced from the container;
    generating alphanumeric intensity data from sensed light intensity; and
    causing transmission of the alphanumeric intensity data to the communication device.

11. The method of claim 10, wherein transmitting feed level data further comprises:
    comparing feed level data to a predetermined threshold level; and
    conditioning transmission of feed level data on inclusion of a value of feed level data that is less than the predetermined threshold level.

12. The method of claim 10, wherein transmitting feed level data further comprises:
   receiving a message from a sender over a second communication link; and
   sending a reply communication to the sender over the second communication link in response to receipt of the message, the reply communication comprising the sensed level of feed.

13. The method of claim 12, wherein transmitting feed level data further comprises:
   processing the message to determine whether the message contains a valid command; and
   conditioning the sending of the reply communication on a determination that the message contains the valid command.

14. The method of claim 10, further comprising:
   sensing temperature and humidity proximate to the container;
   generating temperature and humidity data from the sensed temperature and humidity; and
   transmitting the sensed temperature and humidity data over the first communication link to the communication device.

15. The method of claim 10, further comprising reading power from a power source supplying power to a light intensity sensor.

16. A remote monitoring system, comprising:
   a local module configured to be suspended above a container, the local module comprising
      a local microcontroller,
      a feed level sensor electrically coupled to the local microcontroller, the feed level sensor configured to determine a distance between the feed level sensor and a top feed surface of any feed present in the container, and
      a communication unit electrically coupled to the local microcontroller, the communication unit being configured to exchange data with the local microcontroller and to wirelessly send data to a communication device of a user; and
   a beehive spaced from the local module, the beehive including a remote module, the remote module comprising
      a remote microcontroller,
      a light intensity sensor electrically coupled to the remote microcontroller, the light intensity sensor configured to sense light intensity within the beehive, and
      a transmitter electrically coupled to the remote microcontroller, the transmitter configured to communicate alphanumeric intensity data generated from the light intensity sensed by the light intensity sensor to at least one of the local module and the communication device.

17. A remote monitoring system, comprising:
   a local module configured to be suspended above a container having an internal cavity, the local module comprising
      a local microcontroller,
      a feed level sensor electrically coupled to the local microcontroller, the feed level sensor configured to determine a distance between the feed level sensor and a top feed surface of any feed stored in the internal cavity of the container, and
      a communication unit electrically coupled to the local microcontroller, the communication unit being configured to exchange data with the local microcontroller and to wirelessly send data to a communication device of a user; and
   a remote module configured for placement inside a structure spaced from the local module, the structure configured to house living organisms, the remote module comprising
      a light intensity sensor, the light intensity sensor configured to sense light intensity within the structure,
      a remote microcontroller electrically coupled to the light intensity sensor, the remote microcontroller configured to
         assign an intensity value to the light intensity sensed by the light intensity sensor,
         store the intensity value into a memory of the remote microcontroller, and
         transmit the intensity value to at least one of the local module and the communication device of the user, and
      a remote transmitter electrically coupled to the remote microcontroller, the remote transmitter configured to communicate alphanumeric intensity data generated from the light intensity sensed by the light intensity sensor to at least one of the local module and the communication device;
   wherein the local microcontroller is configured to
      receive the intensity value from the remote transmitter via a local transmitter communicating with the local microcontroller,
      compose a character string corresponding to the intensity value, and
      transmit the character string to the communication device of the user.

* * * * *